United States Patent [19]
Harada et al.

[11] Patent Number: 4,659,709
[45] Date of Patent: Apr. 21, 1987

[54] 2,3-DIHYDROBENZOFURAN-5-SULFONAMIDE DERIVATIVES USEFUL AS ANTIHYPERTENSIVE DIURETIC AGENTS

[75] Inventors: Hiroshi Harada; Yoshihiro Matsushita; Masuhisa Nakamura, all of Osaka; Yukio Yonetani, Nara, all of Japan

[73] Assignee: Shionogi & Co., Osaka, Japan

[21] Appl. No.: 764,785

[22] Filed: Aug. 12, 1985

[30] Foreign Application Priority Data

Sep. 5, 1984 [JP] Japan .................. 59-186971

[51] Int. Cl.⁴ .................. A61K 31/34; C07D 307/85; C07D 307/80
[52] U.S. Cl. .................. 514/229; 514/320; 514/422; 514/469; 514/470; 544/153; 546/196; 548/525; 549/304; 549/462; 549/467; 549/468

[58] Field of Search .............. 549/304, 462, 467, 468; 544/153; 546/196; 548/525; 514/229, 320, 422, 469, 470

[56] References Cited

U.S. PATENT DOCUMENTS

| 4,237,130 | 12/1980 | Cragoe, Jr. et al. | 549/468 |
| 4,401,669 | 8/1983 | Cragoe, Jr. et al. | 549/468 |
| 4,544,667 | 10/1985 | Shepard et al. | 548/525 |
| 4,574,128 | 3/1986 | Seuring et al. | 549/468 |

Primary Examiner—Henry R. Jiles
Assistant Examiner—Bernard I. Dentz
Attorney, Agent, or Firm—Wenderoth, Lind & Ponack

[57] ABSTRACT

Highly effective diuretic antihypertensives, i.e., 2,3-dihydrobenzofuran-5-sulfonamide derivatives which is classified to loop diuretics with less adverse side-effects and can be administered orally at a daily dosage of 0.5–200 mg or parenterally of 0.01–50 mg.

6 Claims, No Drawings

2,3-DIHYDROBENZOFURAN-5-SULFONAMIDE DERIVATIVES USEFUL AS ANTIHYPERTENSIVE DIURETIC AGENTS

BACKGROUND OF THE INVENTION

1. Field of the Invention

The present invention relates to novel compounds having both diuretic and antihypertensive actions, more particularly it relates to 2,3-dihydrobenzofuran-5-sulfonamide derivatives, having remarkable both diuretic and antihypertensive actions with the effect of excretion of uric acid, and to the diuretic antihypertensives containing them.

2. Prior Art

All diuretic antihypertensives are classified, by the actions and the structures thereof, to diuretic thiazides, loop diuretics, and potassium-sparing diuretics such as antialdosterone-type compounds. The dihydrobenzofuransulfonamide derivatives of the present invention can be reasonably classified to loop diuretics. Followings are the representative of loop diuretic agents which are clinically used or are under research and development.

Ethacrynic acid: Edecril ® (Nippon Merck-Banyu),
Chlorthialidone: Hygroton ® (Fujisawa Pharmaceutical Co., Ltd./Ciba-Geigy Japan),
Mefruside: Baycaron ® (Yositomi Pharmaceutical Ind.)
Furosemide: Lasix ® (Hoechst)
Bumetanide: Lunetoron ® (Sankyo Co., Ltd.)
Tienilic acid, or Ticrynafen: U.S. Pat. No. 3,758,506 (C.E.R.P.H.A.), 1
Indacrinone and the relates: Japanese Unexamined Patent Publication Nos. 57-163338, 57-163339, 57-176920, 57-176968, 57-209246 (Merck),
Benzenesulfonamide derivatives substituted at 2, 3, and 4 positions: JPN Unexam. Pub. No. 58-124758 (Fujisawa Pharmaceutical Co., Ltd.),
5-Acyl-substituted-2,3-dihydrobenzofuran derivatives: JPN Unexam. Pub. No. 52-10261 (Merck).

The compounds of this invention are classified to the same family as the compounds finally listed above, i.e., 5-Acyl-substituted-2,3-dihydrobenzofuran derivatives, in their essential structure, but different in their partial structure, i.e., the latter is 5-acyl compound, while the former is sulfonamide one.

SUMMARY OF THE INVENTION

This invention provides for new diuretic sulfonamides which can be administered orally at a daily-dosage of 0.5–200 mg, preferably 1–100 mg or parenterally of 0.01–50 mg, preferably of 0.1–20 mg, and which have the following formula (I):

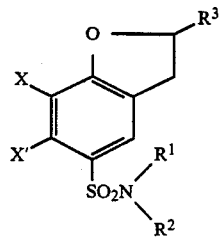

(I)

wherein $R^1$ and $R^2$, which are the same or different each other, each is hydrogen, lower alkyl, 4- to 7-membered cycloalkyl, substituted or unsubstituted phenyl, phenyl(lower alkyl), lower alkoxycarbonyl, or morpholino(lower alkyl); or $R^1$ and $R^2$ may cyclize together with the adjacent nitrogen atom to form a substituted or unsubstituted 5- or 6-membered hetero cycle which may have additional one or more hetero atoms, $R^3$ is a group represented by $COR^4$ or $CH_2R^5$, $R^4$ is hydroxy or a group represented by $OR^6$ or $NR^7R^8$, $R^5$ is hydroxy, lower alkoxy, lower aliphatic acyloxy, or halogen, $R^6$ is lower alkyl, aryl, carboxymethyl or an ester thereof, hydroxymethyl or an aliphatic acylate thereof, or 3-phthalidyl, $R^7$ and $R^8$, which are the same or different each other, each is hydrogen or lower alkyl, and X and X', which are the same or different each other, each is hydrogen or halogen.

DESCRIPTION OF THE PREFERRED EMBODIMENT

Thiazide drugs, which are most frequently used as diuretic antihypertensives except for antialdosterone-type compounds, accelerate the excretion of $Na^+$ and $Cl^-$ by restraining resorption of them at the convoluted tubule of the nephron: this action gives good effect in the light of diuretic effect, but frequently causes various side effects such as hyponatremia, hypokaliemia, glycohemia, uricemia, and the like.

On the other hand, loop diuretic agents cannot be used as a first-choice drug because they occasionally fail in decreasing the blood-pressure, or because the diuretic action of them is short in time although the action is both rapid and potent.

Inconsideration of both advantage and disadvantage of those agents, the present inventors have studied to develop new diuretics to scarcely cause such adverse reactions, especially, as uric acid retention action or the like.

The compounds represented by the formula (I) can, by the properties of the substituents thereof, be acid addition salts or the salts with an alkali metal, alkaline earth metal, organic base or the like. The acid addition salts include, for example, the salts with hydrochloric acid, hydrobromic acid, nitric acid, sulfuric acid, phosphoric acid, perchloric acid, oxalic acid, malonic acid, succinic acid, malic acid, lactic acid, or the like. The salts with a metal or an organic base include, for example, the salts with sodium, potassium, calcium, magnesium, triethylamine, dimethylaniline, N-methylmorpholine, amyloride, or the like.

This invention also provides a diuretic antihypertensive agent containing either a compound of the formula (I) or the salt thereof as an active ingredient.

In the formula (I), the lower alkyl shown by $R^1$ or $R^2$ means straight or branched chain $C_1$–$C_5$ alkyl such as methyl, ethyl, propyl, isopropyl, butyl, s-butyl, isobutyl, pentyl, isopentyl, or the like. Four- to seven-membered cycloalkyl means cyclobutyl, cyclopentyl, cyclohexyl, cycloheptyl, or the like. Substituted phenyl, whose substituent is halo such as fluoro, chloro, or bromo; alkoxy such as methoxy, ethoxy; or the like, includes p-methoxyphenyl, p-chlorophenyl, or the like. Phenyl(lower alkyl), which means the above-identified lower alkyl substituted by phenyl, includes benzyl, phenethyl, phenylpropyl, or the like. Lower alkoxycarbonyl, which means an alkoxycarbonyl formed by oxycarbonyl and the above-identified lower alkyl, includes methoxycarbonyl, ethoxycarbonyl, propoxycarbonyl, butoxycarbonyl, or the like. Morpholino(lower alkyl) means an above-identified lower alkyl which is substituted by morpholino and includes morpholinomethyl, morpholinoethyl, morpholinopropyl, or the like.

Moreover, the substituted or unsubstituted 5- or 6-membered hetero cycle, which is formed by $R^1$ and $R^2$ together with the adjacent nitrogen atom and may have additional one or more hetero atoms, represents pyrrolidino, piperidino, morpholino, or the like, wherein the substituent is lower alkyl.

Lower alkoxy explained in the definition of $R^5$, which indicates an alkoxy formed with the above-identified lower alkyl, includes methoxy, ethoxy, propoxy, isopropoxy, butoxy, isobutoxy, pentyloxy, or the like. Lower aliphatic acyloxy means straight or branched chain $C_1$-$C_5$ acyloxy and includes formyloxy, acetyloxy, propionyloxy, butyryloxy, isobutyryloxy, valeryloxy, isovaleryloxy, pivaroyloxy, or the like. Halogen includes fluorine, chlorine, bromine, or the like.

Lower alkyl defined in $R^6$ definition has the same meaning as in the definition of $R^1$ and $R^2$, wherein aryl includes phenyl, tolyl, xylyl, or the like; and ester of carboxymethyl includes such a lower alkyl ester as methyl ester, ethyl ester, or the like. Aliphatic acyl in the definition of the aliphatic acylate of hydroxymethyl has the same meaning as the acyl moiety of the aliphatic acyloxy group defined above as $R^5$.

Lower alkyl as the definition of $R^7$ or $R^8$ has the same meaning as that in $R^1$ or $R^2$.

Halogen represented by X and X' includes fluoro, chloro, or bromo.

Processes for this invention can be summarized as the following reaction sequence.

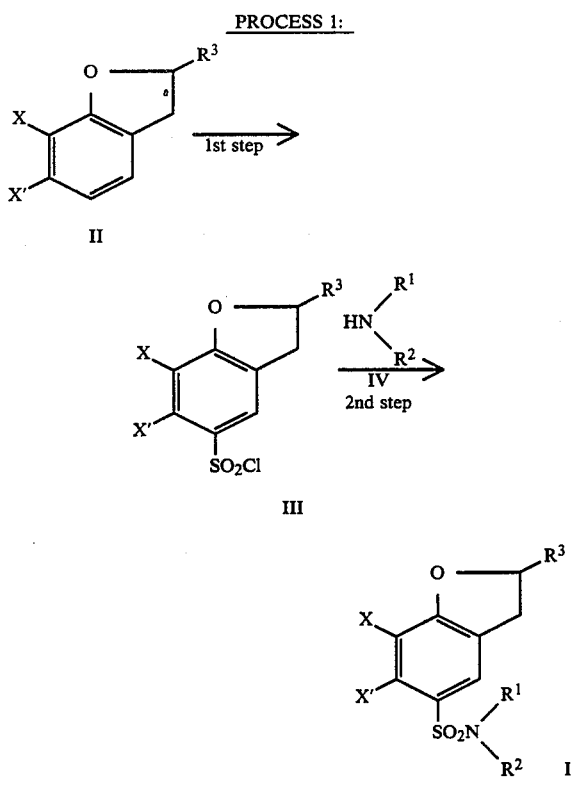

wherein $R^1$, $R^2$, $R^3$, X, and X' have the same meanings as those defined above, respectively.

Preparation of the compounds of the present invention is substantially processed through the above-summarized process 1: there could however be alternative better reactions in preferrance to said reactions in some cases of the substitutions of $R^1$, $R^2$, and $R^3$. The 1st step shown above is recommended particularly when $R^3$ is carboxylic acid ester, alkoxymethyl, or acyloxymethyl. Each step is explained below in detail.

The First Step

A dihydrobenzofuran derivative is chloro-sulfonated selectively at the 5 position of the ring. The reaction can be accomplished by direct sulfonation with such a chlorosulfonating agent as chlorosulfonic acid, sulfur trioxide/sulfuric acid, phosphorus pentoxide/thionyl chloride, or the like; or by chloro-sulfonated with sulforous acid/cupric chloride ($CuCl_2$) via the 5-diazo compound; or the like. The reaction with chlorosulfonic acid is processed under the following conditions; for example, in such a solvent as thionyl chloride, carbon tetrachloride, chloroform, dichloroethane, or the like; at $-10°$ to $70°$ C., preferably at $-5°$ to $50°$ C; for about 1 to 4 hours, preferably for about 1.5 to 2.5 hours. The reaction mixture is poured into water, extracted with a solvent, and the extract dried and then evaporated to give the reaction product, which may be employed for the next step without any purification.

Some of the starting materials II employed for this step are known-compounds disclosed in J. Med. Chem., 24, 865 (1981) by Hoffman et al. and the others can be readily prepared by the manner disclosed in said disclosure.

The Second Step

A 5-chlorosulfonyl compound III prepared through the foregoing step is reacted with ammonia, amine, or carbamic acid derivative represented by the formula IV to give the 5-sufonamide derivative I. It is preferable to carry out the reaction generally in such an organic solvent as alcohols including methanol, ethanol, isopropanol, or the like; halogeno hydrocarbons including dichloromethane, chloroform, dichloroethane, or the like; or ethers including tetrahydrofuran (hereinafter referred to as THF), dioxane, or the like, under cooling or at room temperature, preferably at $-50°$ to $15°$ C., more preferably at $-30°$ to $-20°$ C., for a duration of time between several minutes and several hours, preferably for a duration of 30 minutes to 3 hours. Ammonium carbonate in place of ammonia may be employed for this reaction.

The reaction products can be readily isolated and purified by such usual techniques for isolation and purification as seen in the field of organic chemistry: for example, elution, washing, chromatography, recrystallization or the like. The isolation and purification techniques may be employed for the products in the following steps.

Hydrolysis of carboxylic acid esters

When $R^3$ is carboxylic acid ester in the afore-shown formula I, the ester can be subjected to hydrolysis to form the free acid I ($R^3$=COOH; hereinafter abbreviated as I b). This may be shown by the following scheme.

PROCESS 2:

I(R³ = carboxylic acid ester) ⟶

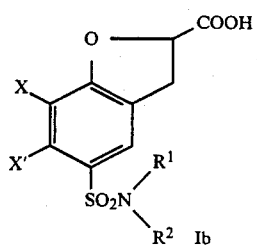

wherein R¹, R², R³, X, and X' have the same meanings as those defined above, respectively.

The reaction of this process may be carried out according to the usual hydrolysis for carboxylic acid esters. For instance, the starting compound may be reacted with an alkali such as sodium carbonate, potassium carbonate, sodium hydroxide, potassium hydroxide, or the like in water or an aqueous mixture of water miscible solvent such as methanol, ethanol, isopropanol, t-butanol, THF, dioxane, acetonitrile, dimethylformamide (hereinafter referred to as DMF), or the like at room temperature or under heating, preferably at 15° to 70° C.

The free acids I b obtained by the hydrolysis may, if needed, be converted to the salts with alkali metal, alkaline earth metal, or organic base as mentioned above.

Esterification of I b

If R³ in the formula I is a special carboxylic acid ester, the alternative process could be better where the free acid I b thereof is prepared in advance of the subsequent esterification. The process can be shown in the following scheme.

PROCESS 3:

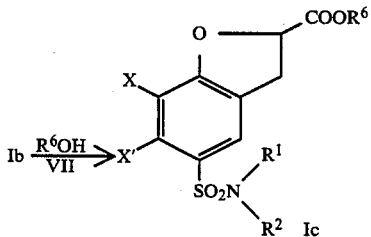

wherein R¹, R², R⁶, X, and X' have the same meanings as those defined above, respectively.

The esterification of this process can be generally carried out according to the processes for esterification of carboxylic acids: for instance, processes that the carboxylic acids I b are converted to the activated forms with acid halide (chloride, bromide, or the like), mixed acid anhydride (acid anhydride obtained by the reaction with ethyl chloroformate, or the like), activated ester (p-nitrophenyl ester, 2,4-dinitrophenyl ester, pentachlorophenyl ester, or the like), and then reacted with alcohols R⁶OH (VII) corresponding to the esters employed; or processes that the acids I b are reacted directly with alcohols VII in the presence of such a suitable condensing agent as dicyclohexylcarbodiimide (DCC) or the like.

To obtain the acid halides of carboxylic acids I b, the acids may be allowed to react in such an inert solvent as benzene, toluene, xylene, or the like at room temperature or under reflux for a duration of time between several ten minutes and several hours by using such a halogenating agent as thionyl chloride, thionyl bromide, phosphorus trichloride, phosphorus pentachloride, phosphorus oxychloride, oxalylchloride, or the like in the presence of such a base as triethylamine, pyridine, dimethylaniline, N-methylmorpholine. The solvent and the remainder of the reagents are removed therefrom to give an acid halide as a residue, which can, without purification, be used for the subsequent condensation with an alcohol VII.

The condensation of acid halides with an alcohol VII is carried out by reflux for a duration of time between several ten minutes and several hours in such an inert solvent as benzene, toluene, ether, THF, or the like, preferably in the presence of an inorganic base (e.g., sodium carbonate, potassium carbonate) or an organic base (e.g., triethylamine, pyridine, dimethylaminopyridine), under cooling or at room temperature. When an alcohol VII is phenol, its alkali metal salts, for example, salts with sodium, potassium, or the like can be employed: where no base is required for this reaction.

PROCESS 4:

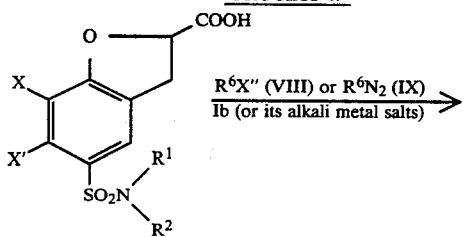

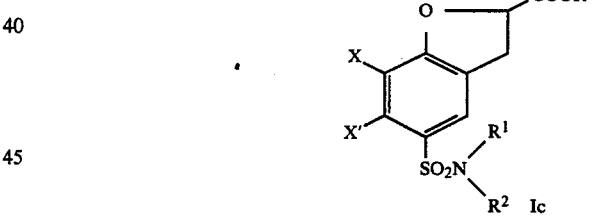

wherein X" is a halogen atom such as chloro, bromo, or iodo; and R¹, R², R⁶, X, and X' have the same meanings as those defined above, respectively.

The reaction of the carboxylic acids I b or the alkali metal salts thereof with halides R⁶X" (VII) or diazoalkanes R⁶N₂ (IX) can be employed as an alternative process for preparation of the ester derivatives I c. For instance, halides VII is generally reacted with the alkali metal salts (sodium, potassium, or the like) of the carboxylic acids I b. This reaction may be carried out at room temperature or at reflux temperature in such a polar solvent as methanol, ethanol, acetonitrile, DMF, dimethylsulfoxide (hereinafter referred to as DMSO), or the like.

On the reaction with diazoalkanes IX, the carboxylic acids I b is employed as the free acids for the reaction, which is carried out generally under cooling or at room temperature in an ethereal solvent including ether, THF, or the like, or in a halogenated hydrocarbon including dichloromethane, dichloroethane, or the like.

Representatives of the diazoalkanes IX are diazomethane, diazoethane, ethyl diazoacetate, diphenyldiazomethane, and the like.

Preparation of carboxylic acid amide

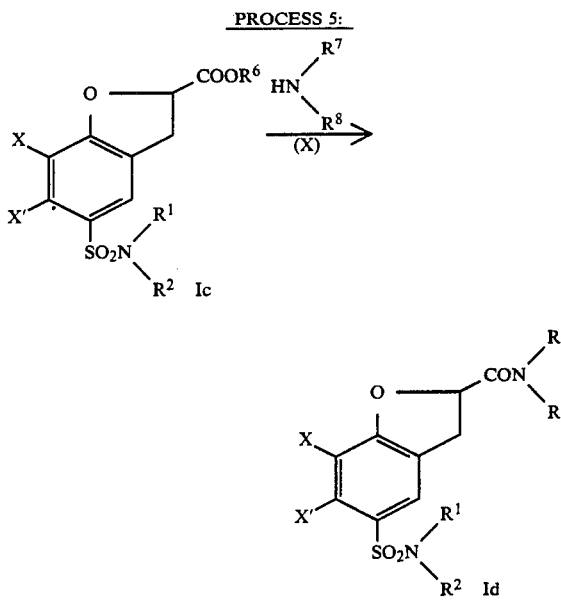

wherein $R^1$, $R^2$, $R^6$, $R^7$, $R^8$, X, and X' have the same meanings as those defined above, respectively.

A carboxylic acid ester is reacted with a compound of formula X such as monoalkylamine, dialkylamine, ammonia, or the like to give the corresponding carboxylic acid amide I d. In this reaction, it is better that the substituent $R^6$ of the esters I c is lower alkyl such as methyl, ethyl, or the like; or aryl such as phenyl, tolyl, or the like. The reaction is carried out in an alcoholic solvent such as methanol, ethanol, or the like, at room temperature for 10 to 30 hours. The reaction may be subjected to the conditions under heating to make the reaction time shorter.

As an alternative approach, the carboxylic acids I b may, as mentioned concerning the reaction in the Process 3, be converted to the acid halides which may be then reacted with the amines or ammonia mentioned above.

Alkylation or Acylation of Sulfonamide

When either $R^1$ or $R^2$ is hydrogen in the formula I, alkylation or acylation can be accomplished at the N-position of the sulfonamides. It may be better for the procedures for the alkylation or acylation that the sulfonamides is converted to the salts with lithium or sodium by reaction with lithium hydride, sodium hydride, sodium amide, or the like at the N-H, and the salts is subjected to the reaction with an alkylating agent (ethyl bromide, propyl bromide, or the like) or an acylating agent (ethyl chloroformate or the like). The reaction is generally carried out in an aprotic polar solvent such as tetrahydrofuran, acetonitrile, DMSO, DMF, or the like, at $-30°$ to $50°$ C. preferably at a temperature between ice-cooling temperature and room temperature, for 1 to 3 hours. It is needless to say that if there is any susceptible functional group in the molecular of the compound, those reactions should be carried out after it is protected by a suitable protecting group.

Compounds Ii wherein $R^3$ is $CH_2OH$

The compounds where $R^3$ is $CH_2OH$ in the formula I may be prepared directly from the starting matrials II ($R^3 = CH_2OH$) according to the manner explained in the Process 1; or from the comounds I ($R^3 =$ lower aliphatic acyloxymethyl) by hrdrolysis as shown in the following scheme.

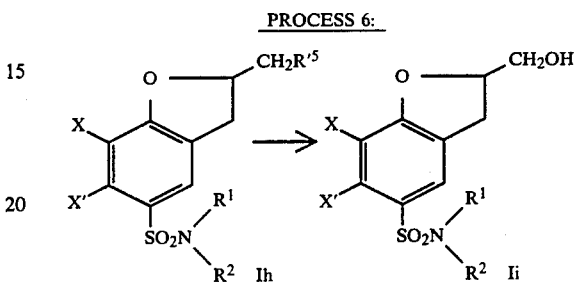

wherein $R'^5$ is aliphatic acyloxy, and $R^1$, $R^2$, X, and X' have the same meanings as those defined above, respectively.

The hydrolysis can be subjected to the same conditions as the hydrolysis for the carboxylic acid esters explained in the Process 2.

Etherification of I i

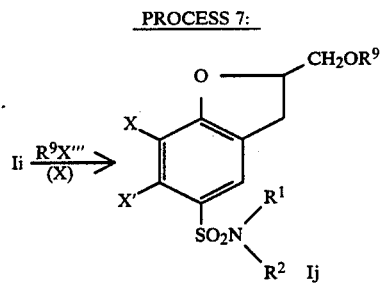

Wherein $R^9$ is lower alkyl, X''' is halogen atom, and $R^1$, $R^2$, X, and X' have the same meanings as those defined above, respectively.

The compounds I i are treated with lithium hydride, sodium hydride, sodium amide, or the like to form, at the position of hydroxy, their alkali metal salts such as lithium salts, sodium salts, or the like, which is then reacted with halogenated alkyls $R^9X'''$ (XI) to give the ether derivatives I j. The reaction may be carried out in such an aprotic solvent as ether, THF, DMF, DMSO, acetonitrile, or the like at $-30°$ to $50°$ C. preferably between under ice-cooling and at room temperature, for 10 to 30 hours.

The ether derivatives I j can be also prepared from the compounds II ($R^3 =$ lower alkoxymethyl) in the same manner as in the Process 1.

Halogenation of I i

PROCESS 8:

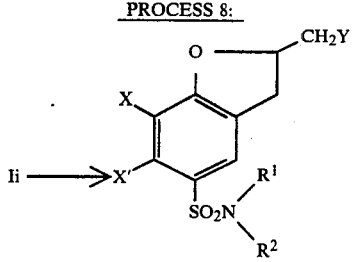

Wherein Y is halogen atom; and $R^1$, $R^2$, X, and X' have the same meanings as those defined above, respectively.

The hydroxy compounds I i are treated with a halogenating agent to form their halogenated derivatives I k. The reaction may be carried out under the same conditions as usual halogenation of alcohols where, for example, thionyl chloride, thionyl bromide, phosphorus trichloride, phosphorus tribromide, phosphorus pentachloride, phosphorus pentabromide, phophorus oxychloride, phosphorus oxybromide, or the like is employed as the halogenating agent. Furthermore, the reaction may be carried out in such a solvent as benzene, toluene, xylene, THF, chloroform, dichloromethane, dichloroethane, DMF, pyridine, N-methylmorpholine at room temperature or under heating.

In the foregoing reactions, it is a matter of course that a specific functional group may, if necessary, be protected in a conventional manner and unnecessary one may, in traverse, be removed: where both the selection of the protecting group employed and the manner for protection or removal of them are well known to a person ordinary skilled in the art.

EXAMPLE 1

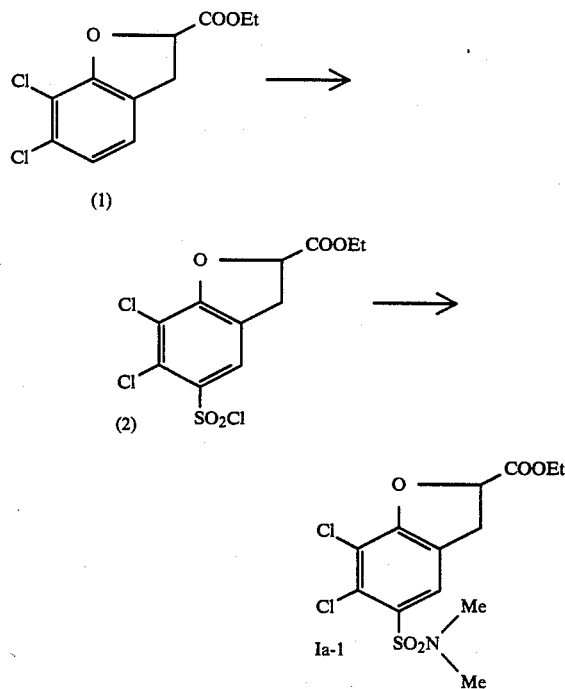

To a solution (2.5 ml) of 1 g (3.83 mmol) of ethyl 6,7-dichloro-2,3-dihydrobenzofuran-2-carboxylate (1) in 2.5 ml of thionyl chloride is dropwise added 1.25 g of chlorosulfonic acid under ice-cooling and the mixture allowed to react at room temperature for 2 hours. The reaction mixture is poured into iced water and extracted with 60 ml of ethyl acetate. The organic layer is dried and evaporated to give about 1.4 g of ethyl 5-chlorosulfonyl-6,7-dichloro-2,3-dihydrobenzofuran-carboxylate (2) as an oil.

A solution of the oily product dissolved in 8 ml of dichloromethane is cooled to a temperature between $-30°$ and $-20°$ C., to which 30% of ethanol solution of dimethylamine [0.518 g (3.83×3 mmol)] is dropwise added, and then allowed to react for one hour. After the completion of the reaction is checked by thin layer chromatography (hereinafter referred to as TLC) (silica gel/dichloromethane), the reaction mixture is adjusted to about pH 5 and then extracted with dichloromethane. The organic layer is dried, evaporated under reduced pressure to leave an oily residue, which is chromatographed on silica gel (dichloromethane as an eluent) for purification to give 1.0 g of ethyl 5-(N,N-dimethylsufamoyl)-6,7-dichloro-2,3-dihydrobenzofuran-2-carboxylate as a crystalline product (71% yield), m.p. 124°–125° C.

Analysis Calcd (%) for $C_{13}H_{15}NSCl_2O_5$: C, 42.40; H, 4.11; N, 3.80; S, 8.71; Cl, 19.26. Found (%): C, 42.11; H, 4.19; N, 3.82; S, 8.61; Cl, 19.28.

NMR (d6-acetone) δppm: 1.33 (t, 3H, J=7.0), 2.90 (s, 6H), 3.30–3.90 (m, 2H), 4.31 (q, 2H, J=7.0), 5.40 (dd, 1H, J=10 and 7.0), 7.88 (t, 1H, J=1.0).

EXAMPLES 2–27

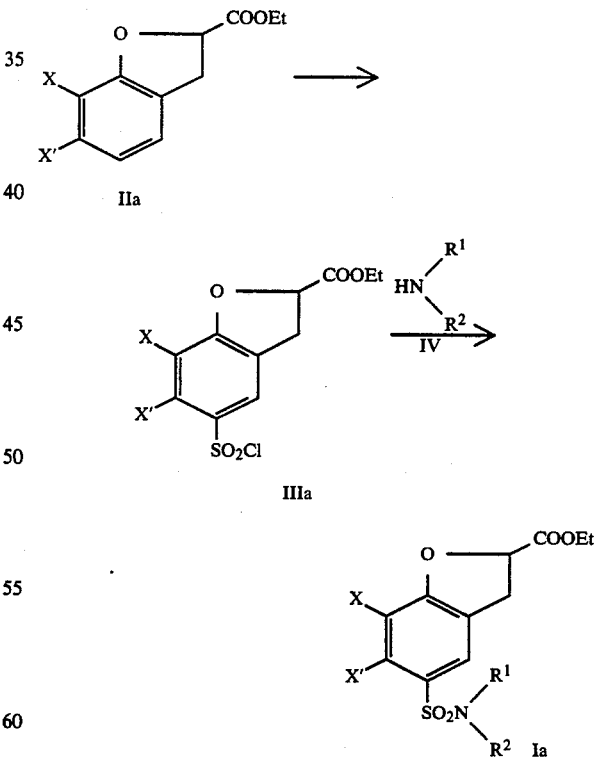

To a solution of 3.83 mmol of a 6,7-dichloro-2,3-dihydrobenzofuran derivative (II a) dissolved in 2.5 ml of thionyl chloride is dropwise added 1.25 g of chlorosulfonic acid under ice-cooling and then allowed to react for 2 hours at room temperature. The reaction mixture is poured into iced-water, then extracted with 60 ml of ethyl acetate. The organic layer is dried and evaporated to give a 5-chlorosulfonyl compound (III a). A solution of the compound (III a) dissolved in about 8 ml of dichloromethane is cooled to a temperature between −30° C. and −20° C., to which about 11.5 mmol of the corresponding ammonia or amine is added, and the resulting mixture is allowed to react for 0.5 to 3 hours. After the completion of the reaction is checked through TLC, the mixture is adjusted to about pH 5 by addition of dichloromethane and extracted with dichloromethane. The organic layer is washed with water, dried, and evaporated to give a product, which is then purified by chromatography (column on silica gel) and confirmed to be an objective 5-sulfamoyl-6,7-dichlorobenzofuran derivative (I a). The reaction conditions in each step and the physical properties of the products are summarized on the tables 1 and 2.

TABLE 1

| Compd. Ia | Substituent | | | | Reaction Conditions | | Chromatography | Yield |
|---|---|---|---|---|---|---|---|---|
| | X | X' | $R_1$ | $R_2$ | Temp. °C. | Time (hr) | Solvent | % |
| 2 | Cl | Cl | H | H | −30 | 2 | Ether/$CH_2Cl_2$ (1:20) | 50 |
| 3 | " | " | $C_2H_5$ | $C_2H_5$ | −30 | 1.5 | $CH_2Cl_2$ | 70 |
| 4 | " | " | $CH_2CH_2CH_3$ | $CH_2CH_2CH_3$ | −35 | 0.5 | $CH_2Cl_2$ | 75 |
| 5 | " | " | $CH(CH_3)_2$ | $CH(CH_3)_2$ | −35/r.t. | 3/overnight | $CH_2Cl_2$ | 28 |
| 6 | " | " | $CH_3$ | $CH_2CH_2CH_2CH_3$ | −20 | 1.5 | $CH_2Cl_2$:n-hexane (1:1) | 85 |
| 7 | " | " | —$CH_2C_6H_5$ | —$CH_2C_6H_5$ | −20/r.t. | 1/1.5 | $CH_2Cl_2$ | 75 |
| 8 | " | " | $CH_3$ | —$CH_2C_6H_5$ | −30 | 2 | $CH_2Cl_2$ | 76 |
| 9 | " | " | $CH_3$ | $C_6H_5$ | −30 | 2.5 | $CH_2Cl_2$ | 50 |
| 10 | " | " | $CH_3$ | cyclohexane | −20 | 1.5 | $CH_2Cl_2$ | 73 |
| 11 | " | " | —$(CH_2)_4$— | | −20 | 1.5 | $CH_2Cl_2$ | 56 |
| 12 | " | " | —$(CH_2)_5$— | | −20 | 1 | $CH_2Cl_2$ | 67 |
| 13 | " | " | —$CH_2$—$CH_2$—O—$CH_2$—$CH_2$— | | −30 | 1.5 | $CH_2Cl_2$ | 70 |
| 14 | " | " | H | $CH_3$ | −30 | 1 | $CH_2Cl_2$ | 75 |
| 15 | " | " | H | —$CH_2CH_2CH_3$ | −30 | 1 | $CH_2Cl_2$ | 70 |
| 16 | " | " | H | —$CH(CH_3)_2$ | −20 | 1 | $CH_2Cl_2$:n-hexane (1:1) | 80 |
| 17 | " | " | H | —$CH_2C_6H_5$ | −30 | 1 | $CH_2Cl_2$ | 73 |
| 18 | " | " | H | $C_6H_5$ | −30 | 2 | $CH_2Cl_2$:n-hexane (2:1) | 64 |
| 19 | " | " | H | p-Cl—$C_6H_4$— | −20/r.t. | 48/48 | $CH_2Cl_2$:n-hexane (2:1) | 58 |
| 20 | " | " | H | p-$CH_3O$—$C_6H_4$— | −20/r.t. | 1/48 | $CH_2Cl_2$ | 80 |
| 21 | " | " | H | morphorinoethyl | −30~−10 | 3 | $CH_2Cl_2$:acetone (20:1) | 53 |
| 22 | Cl | H | $CH_3$ | $CH_3$ | −30 | 1 | ethyl acetate/hexane (recrys) | 81 |
| 23 | Cl | H | $C_2H_5$ | $C_2H_5$ | −30 | 0.5 | $CH_2Cl_2$:ether (20:1) | 76 |
| 24 | H | Cl | $CH_3$ | $CH_3$ | −30 | 1 | $CH_2Cl_2$:acetone (100:1) | 36 |
| 25 | H | Cl | $C_2H_5$ | $C_2H_5$ | −30 | 1 | $CH_2Cl_2$:acetone (100:1) | 37 |
| 26 | Br | H | $CH_3$ | $CH_3$ | −30 | 1.5 | $CH_2Cl_2$:ether (20:1) | 81 |
| 27 | Br | H | $C_2H_5$ | $C_2H_5$ | −30 | 1 | $CH_2Cl_2$:ether (20:1) | 79 |

TABLE 2

| Cmpd. Ia | Melting Point °C. | Molecular formula (molecular Weight) | Elementary Analysis (%) | | | | NMR δ ppm (J Hz) |
|---|---|---|---|---|---|---|---|
| | | | C | H | N | S Cl | |
| 2 | 167~168 | $C_{11}H_{10}NO_5Cl_2S$. ½ $H_2O$ (348.181) | 37.94 38.27 | 3.18 3.09 | 4.02 4.13 | 9.21 9.18 | ($d_6$-acetone): 1.25 (3H, t, J = 7.2), 3.45~4.05 (2H, m), 4.21 (2H, q, J = 7.2), 5.51 (1H, dd, J = 10.1 & 6.5), 6.62 (2H, b s), 7.87 (1H, t, J = 1.2) |
| 3 | Oil | $C_{15}H_{19}NSCl_2O_5$ (396.292) | 45.46 45.08 | 4.83 4.76 | 3.53 3.58 | 8.09 17.89 8.21 18.56 | ($CDCl_8$): 1.12 (6H, t, J = 7.0), 1.30 (3H, t, J = 7.0), 3.32 (4H, q, J = 7.0), 3.10~3.90 (2H, m), 4.25 (2H, q, J = 7.0), 5.35 (1H, dd, J = 10 & 7.0), 7.86 (1H, t, J = 1.0) |
| 4 | 87~88 | $C_{17}H_{28}NSCl_2O_5$ (424.347) | 48.12 47.98 | 5.46 5.41 | 3.30 3.40 | 7.56 16.71 7.64 16.81 | ($CDCl_8$): 0.83 (6H, t, J = 7.0), 1.31 (3H, t, J = 7.0), 1.40~1.80 (4H, m), 3.00~4.00 (2H, m), 4.30 (2H, q, J = 7.0), 5.38 (1H, dd, J = 10 & 7.0), 7.92 (1H, t, J = 1.0) |
| 5 | Oil | $C_{17}H_{28}NSCl_2O_5$. ½ $H_2O$ (433.355) | 47.11 47.24 | 5.58 5.36 | 3.23 3.38 | 7.40 7.45 | ($CDCl_8$): 1.28 (12H, d, J = 7.0), 1.30 (3H, t, J = 7.0), 3.25~4.00 (4H, m), 4.26 (2H, q, J = 7.0) 5.35 (1H, dd, J = 10 & 7.0), 7.90 (1H, t, J = 1.0) |
| 6 | Oil | $C_{16}H_{21}NSCl_2O_6$ (410.319) | 46.84 46.77 | 5.16 5.21 | 3.41 3.32 | 7.81 17.28 7.54 17.47 | ($CDCl_8$): 0.90 (3H, t, J = 7.0), 1.31 (3H, t, J = 7.0), 1.10~1.75 (4H, m), 2.85 (3H, s), 3.22 (2H, t, J = 7.0) 3.30~3.85 (2H, m), 4.28 (2H, q, J = 7.0), 5.37 (1H, dd, J = 10 & 7.0), 7.88 (1H, t, J = 1.0) |
| 7 | Oil | $C_{25}H_{28}NSO_5Cl_2$. ½ $H_2O$ (529.444) | 56.71 56.96 | 4.57 4.51 | 2.65 2.72 | 6.06 6.02 | ($CDCl_8$): 1.31 (3H, t, J = 7.0), 3.20~3.80 (2H, m), 4.26 (2H, q, J = 7.0), 4.37 (4H, s), 5.35 (1H, dd, J = 10 & 7.0), 7.00~7.36 (10H, m), 7.78 (1H, t, J = 1.0) |
| 8 | 102~103 | $C_{19}H_{19}NSCl_2O_6$ (444.337) | 51.36 51.11 | 4.31 4.18 | 3.15 3.21 | 7.22 15.96 7.38 16.13 | ($CDCl_8$): 1.32 (3H, t, J = 7.0), 2.75 (3H, s), 3.26~3.93 (2H, m), 6.30 (2H, q, J = 7.0), 6.42 (2H, s), 5.38 (1H, dd, J = 10 & 7.0), 7.35 (5H, s), 7.92 (1H, t, J = 1.0) |
| 9 | Oil | $C_{18}H_{17}NSCl_2O_6$. $H_2O$ (448.325) | 48.22 48.47 | 4.27 3.95 | 3.12 3.24 | 7.15 6.97 | ($CDCl_8$): 1.28 (3H, t, J = 7.0), 3.13~3.80 (2H, m), 3.38 (3H, s), 4.24 (2H, q, J = 7.0), 5.32 (1H, dd, J = 10 & 7.0), 7.25 (5H, s), 7.63 (1H, t, J = 1.0) |
| 10 | Oil | $C_{18}H_{28}NSCl_2O_6$ | 49.55 | 5.31 | 3.21 | 7.35 16.25 | ($CDCl_8$): 1.30 (3H, t, J = 7.0), 0.8~1.9 |

TABLE 2-continued

| Cmpd. Ia | Melting Point °C. | Molecular formula (molecular Weight) | Elementary Analysis (%) | | | | NMR δ ppm (J Hz) |
|---|---|---|---|---|---|---|---|
| | | | C | H | N | S | |
| | | (436.358) | 49.37 | 5.28 | 3.29 | 7.17 | 16.24 (10H, b), 2.77 (3H, s), 3.20~3.86 (3H, m), 4.25 (2H, q, J = 7.0), 5.35 (1H, dd, J = 10 & 7.0), 7.86 (1H, t, J = 1.0) |
| 11 | 135~136 | C₁₅H₁₇NSCl₂O₆ (394.276) | 45.70 / 45.40 | 4.35 / 4.27 | 3.55 / 3.52 | 8.13 / 7.95 | 17.98 / 18.24 (CDCl₃): 1.31 (3H, t, J = 7.0), 1.80~2.10 (4H, m), 3.30~3.55 (4H, m), 3.30~3.90 (2H, m), 4.28 (2H, q, J = 7.0), 5.37 (1H, dd, J = 10 & 7.0), 7.88 (1H, t, J = 1.0) |
| 12 | 131~132 | C₁₆H₁₉NSCl₂O₅ (408.303) | 47.07 / 46.96 | 4.69 / 4.67 | 3.43 / 3.31 | 7.85 / 7.65 | 17.37 / 17.50 (CDCl₃): 1.33 (3H, t, J = 7.0), 1.59 (6H, b), 3.26 (4H, b), 3.30~3.93 (2H, m), 4.30 (2H, q, J = 7.0), 5.38 (1H, dd, J = 10 & 7.0), 7.86 (1H, t, J = 1.0) |
| 13 | 141~142 | C₁₅H₁₇NSCl₂O₆ (410.275) | 43.91 / 43.45 | 4.18 / 4.03 | 3.41 / 3.48 | 7.82 / 7.76 | (CDCl₃): 1.32 (3H, t, J = 7.0), 3.20~4.00 (10H, m), 4.30 (2H, q, J = 7.0), 5.40 (1H, dd, J = 10 & 7.0), 7.84 (1H, t, J = 1.0) |
| 14 | 140~141 | C₁₂H₁₈NSCl₂O₅ (354.212) | 40.69 / 40.62 | 3.70 / 3.70 | 3.95 / 3.96 | 9.05 / 9.00 | 20.02 / 20.13 (CDCl₃): 1.31 (3H, t, J = 7.0), 8.63 (3H, d, J = 5.0), 3.30~3.93 (2H, m), 4.30 (2H, q, J = 7.0), 5.03 (1H, q, J = 5.0), 5.41 (1H, dd, J = 10 & 7.0), 7.88 (1H, t, J = 1.0) |
| 15 | 102~103 | C₁₄H₁₇NSCl₂O₅ (382.265) | 43.99 / 43.88 | 4.48 / 4.46 | 3.66 / 3.69 | 8.39 / 8.24 | 18.55 / 18.77 (CDCl₃): 0.88 (3H, t, J = 7.0), 1.33 (3H, t, J = 7.0), 1.20~1.70 (2H, m), 2.78 (2H, q, J = 7.0), 3.30~3.90 (2H, m), 4.30 (2H, q, J = 7.0), 5.05 (1H, t, J = 7.0), 5.41 (1H, dd, J = 10 & 7.0), 7.90 (1H, t, J = 1.0) |
| 16 | 169~170 | C₁₄H₁₇NSCl₂O₅ (382.265) | 43.99 / 43.60 | 4.48 / 4.41 | 3.66 / 3.67 | 8.39 / 8.17 | 18.55 / 19.03 (d₆-acetone): 1.06 (6H, d, J = 7.0), 1.26 (3H, t, J = 7.0), 3.20~4.00 (3H, m), 4.25 (2H, q, J = 7.0), 5.56 (1H, dd, J = 10 & 7.0), 6.53 (1H, d, J = 7.0), 7.92 (1H, t, J = 1.0) |
| 17 | 167.5~168.5 | C₁₈H₁₇NSCl₂O₅ (430.310) | 50.24 / 49.96 | 3.98 / 3.98 | 3.26 / 3.27 | 7.45 / 7.33 | 16.48 / 16.80 (CDCl₃): 1.33 (3H, t, J = 7.0), 3.23~3.86 (2H, m), 4.10 (2H, d, J = 5.0), 4.31 (2H, q, J = 7.0), 5.35 (1H, t, J = 5.0), 5.38 (1H, dd, J = 10 & 7.0), 7.25 (5H, s), 7.80 (1H, t, J = 1.0) |
| 18 | 141~142 | C₁₇H₁₅NSCl₂O₅ (416.284) | 49.05 / 48.93 | 3.63 / 3.66 | 3.36 / 3.43 | 7.70 / 7.61 | 17.03 / 17.37 (d₆-acetone): 1.23 (3H, t, J = 7.0), 3.30~3.97 (2H, m), 4.23 (2H, q, J = 7.0), 5.53 (1H, dd, J = 10 & 7.0), 6.90~7.50 (5H, m), 7.95 (1H, t, J = 1.0) |
| 19 | 164~165 | C₁₇H₁₄NSCl₃O₅ (450.729) | 45.30 / 44.91 | 3.13 / 3.13 | 3.11 / 2.94 | 7.11 / 7.05 | 23.60 / 23.89 (d₆acetone): 1.26 (3H, t, J = 7.0), 3.20~4.00 (2H, m), 4.20 (2H, q, J = 7.0), 5.52 (1H, dd, J = 10 & 7.0), 7.25 (4H, s), 7.91 (1H, t, J = 1.0) |
| 20 | 109~110 | C₁₈H₁₇NSCl₂O₆ (446.309) | 48.44 / 48.33 | 3.84 / 3.84 | 3.14 / 3.15 | 7.18 / 7.11 | 15.89 / 15.92 (d₆-acetone): 1.23 (3H, t, J = 7.0), 3.20~3.95 (2H, m), 4.18 (2H, q, J = 7.0), 5.50 (1H, dd, J = 10 & 7.0), 6.75, 7.14 (4H, ABq, J = 9.0), 7.77 (1H, t, J = 1.0), 8.90 (1H, b) |
| 21 | Oil | C₁₇H₂₂N₂SCl₂O₆·½H₂O (462.349) | 44.16 / 44.04 | 5.04 / 4.87 | 6.05 / 5.88 | | (CDCl₃): 1.31 (3H, t, J = 7.0), 2.20~2.60 (6H, m), 3.00 (2H, t, J = 5.0), 3.25~4.00 (6H, m), 4.30 (2H, q, J = 7.0), 5.42 (1H, dd, J = 10 & 7.0), 5.85 (1H, b), 7.87 (1H, t, J = 1.0) |
| 22 | 74~75 | C₁₃H₁₆NO₅ClS (333.790) | 46.78 / 46.74 | 4.83 / 4.80 | 4.20 / 4.06 | 9.60 / 9.84 | 10.62 / 10.39 (CDCl₃): 1.31 (3H, t, J = 7.0), 2.71 (6H, s), 3.46 (1H, dd, J = 16.6 & 7.5), 3.71 (1H, dd, J = 16.6 & 9.8), 4.28 (2H, q, J = 7.0), 5.36 (1H, dd, J = 9.8 & 7.5), 7.49 (1H, b s), 7.64 (1H, b s) |
| 23 | Oil | C₁₅H₂₀NO₅ClS (361.844) | 49.79 / 49.62 | 5.57 / 5.56 | 3.87 / 3.85 | 8.86 / 8.72 | 9.80 / 9.99 (CDCl₃): 1.13 (6H, t, J = 7.2), 1.30 (3H, t, J = 7.1), 3.22 (4H, q, J = 7.2), 3.44 (1H, dd, J = 17.4 & 7.5), 3.70 (1H, dd, J = 17.4 & 10.0), 4.28 (2H, q, J = 7.1), 5.34 (1H, dd, J = 10.0 & 7.5), 7.51 (1H, m), 7.67 (1H, m) |
| 24 | 42~43 | C₁₃H₁₆NO₆ClS (333.794) | 46.78 / 46.69 | 4.83 / 4.61 | 4.20 / 4.22 | 9.61 / 9.59 | 10.62 / 10.80 (CDCl₃): 1.30 (3H, t, J = 7.2), 2.86 (6H, s), 3.20~3.80 (2H, m), 4.27 (2H, q, J = 7.2), 5.30 (1H, dd, J = 10.2 & 7.0), 7.01 (1H, s), 7.88 (1H, t, J = 1.2) |
| 25 | Oil | C₁₅H₂₀NO₅ClS (361.841) | 49.79 / 49.66 | 5.57 / 5.29 | 3.87 / 3.89 | 8.86 / 8.84 | 9.80 / 9.96 (CDCl₃): 1.11 (6H, t, J = 7.1), 1.30 (3H, t, J = 7.1), 3.17~3.75 (6H, m), 4.25 (2H, q, J = 7.1), 5.27 (1H, dd, J = 10.2 & 7.5), 6.97 (1H, s), 7.91 (1H, t, J = 1.2) |
| 26 | 96.5~97.5 | C₁₃H₁₆NO₅BrS (378.246) | 41.28 / 41.19 | 4.26 / 4.29 | 3.70 / 3.78 | 8.48 / 8.40 | Br 21.13 / 21.04 (CDCl₃): 1.31 (3H, t, J = 7.1), 2.72 (6H, s), 3.49 (1H, dd, J = 16.3 & 7.2), 3.75 (1H, dd, J = 16.3 & 9.9), 4.28 (2H, q, J = 7.1), 5.36 (1H, dd, J = 9.9 & 7.2), 7.53 (1H, m), 7.79 (1H, m) |
| 27 | Oil | C₁₅H₂₀NO₅BrS (406.300) | 44.34 / 44.34 | 4.96 / 4.96 | 3.45 / 3.53 | 7.89 / 7.76 | 19.67 / 20.00 (CDCl₃): 1.13 (6H, t, J = 7.0), 1.30 (3H, t, J = 7.2), 3.22 (4H, q, J = 7.0), 3.47 (1H, dd, J = 16.2 & 7.3), 3.72 (1H, dd, |

TABLE 2-continued

| Cmpd. Ia | Melting Point °C. | Molecular formula (molecular Weight) | Elementary Analysis (%) | | | | NMR δ ppm (J Hz) |
|---|---|---|---|---|---|---|---|
| | | | C | H | N | S | |
| | | | | | | | J = 16.2 & 9.9), 4.28 (2H, q, J = 7.2), 5.34 (1H, dd, J = 9.9 & 7.3), 7.55 (1H, m), 7.81 (1H, m) |

EXAMPLE 28

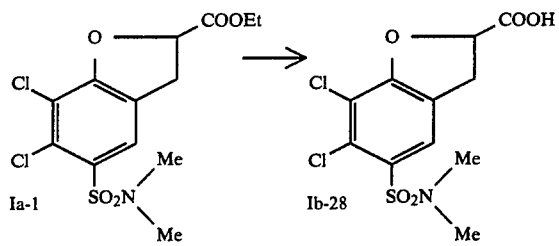

To a solution of 1 g of ethyl 5-(N,N-dimethylsulfamoyl)-6,7-dichloro-2,3-dihydrobenzofuran-2-carboxylate (Ia-1) dissolved in 9 ml of tetrahydrofuran is added 14 ml of 15% aqueous potassium carbonate and the mixture stirred for 72 hours at room temperature. The reaction mixture is condensed under reduced pressure to leave residue, which is made acid (pH 5.0) with 10% hydrochloric acid and extracted with ethyl acetate. The organic layer is dried and evaporated under reduced pressure to leave an oil, which is then recrystallized from either to give 0.868 g of 5-(N,N-dimethylsulfamoyl)-6,7-dichloro-2,3-dihydrobenzofuran-2-carboxylic acid (I b-28), yielded in 94%, m.p. 154° C.

Analysis Calcd (%) for $C_{11}H_{11}NO_5CL_2S$: C, 38.84; H, 3.26; N, 4.12; Cl, 20.84; S, 9.43. Found (%): C, 38.64; H, 2.99; N, 4.31; Cl, 20.92; S, 9.66.

NMR (d$_6$-acetone) δppm: 2.85 (s, 6H), 3.30–4.00 (m, 2H), 5.55 (q, 1H, J=10 and 7), 7.87 (t, 1H, J=1.0), 8.40 (b, 1H).

EXAMPLES 29–54

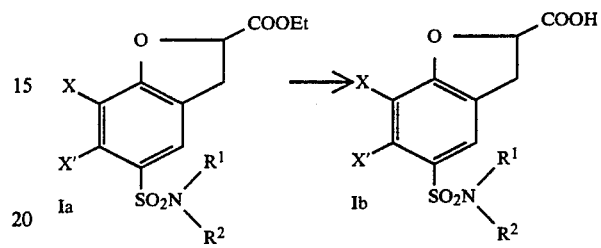

To a solution of 1 g of a compound (I a) obtained in each of Examples 2 to 21 dissolved in 8 to 12 ml of tetrahydrofuran (THF) is added 8 to 20 ml of 15% aqueous potassium carbonate, and the mixture stirred at room temperature. The reaction mixture is evaporated to dryness under reduced pressure after the completion of the reaction is confirmed through TLC. The resulting residue is made acid (pH 5.0) with 10% hydrochloric acid and extracted with ethyl acetate. The organic layer is dried and then evaporated under reduced pressure to leave an oil, which is recrystallized from water, ether and/or n-hexane to give an objective 5-sulfamoyl-6,7-dichlorobenzofuran-2-carboxylic acid (I b) as a free acid. When the free acid is noncrystalline, it can be converted to and isolated as the potassium salt or sodium salt thereof by means that it is dissolved in acetonitrile and conbined with an aqueous solution of potassium carbonate or sodium hydroxide in quantity over equivalent mole to precipitate crystals. The reaction conditions and physical properties on each product are summarized on tables 3 and 4.

TABLE 3

| Compd Ib | Substituent | | | | Reaction Conditions | | | | Solvent for Recrystallization | Yield % | Note |
|---|---|---|---|---|---|---|---|---|---|---|---|
| | X | X' | R₁ | R₂ | 15% K₂CO₈ (ml) | THF (ml) | Temp °C. | Time (hr) | | | |
| 29 | Cl | Cl | H | H | 14 | 9 | r.t.² | 72 | ether/n-hexane | 91 | |
| 30 | " | " | C₂H₅ | C₂H₅ | 16 | 8 | " | 17 | water | 96 | K—salt |
| 31 | " | " | CH₃CH₂CH₂— | CH₃CH₂CH₂— | 16 | 12 | " | 48 | ether/n-hexane | 84 | |
| 32 | " | " | CH₃CHCH₃ | CH₃CHCH₃ | 20 | 20 | " | 23 | ether/n-hexane | 80 | |
| 33 | " | " | CH₉ | CH₃CH₂CH₂CH₂— | 14 | 8 | " | 17 | n-hexane | 76 | |
| 34 | " | " | —CH₂C₆H₅ | —CH₂C₆H₅ | 18 | 10 | " | 17 | ether/n-hexane | 72 | |
| 35 | " | " | CH₃ | —CH₂C₆H₅ | 16 | 12 | " | 48 | ether | 80 | |
| 36 | " | " | CH₃ | C₆H₅ | 10 | 8 | " | 17 | ether | 80 | K—salt |
| 37 | " | " | CH₃ | cyclohexane | 18 | 10 | " | 17 | ether/n-hexane | 52 | |
| 38 | " | " | —(CH₂)₄— | | 10 | 10 | " | 17 | ether | 100 | |
| 39 | " | " | —(CH₂)₅— | | 12 | 10 | " | 17 | ether/n-hexane | 100 | |
| 40 | " | " | —(CH₂)₂—O—(CH₂)₂— | | 16 | 12 | " | 48 | water | 89 | |
| 41 | " | " | H | CH₃ | 15 | 9 | " | 17 | ether | 88 | |
| 42 | " | " | H | CH₉CH₂CH₂— | 14 | 8 | " | 17 | ether/n-hexane | 95 | |
| 43 | " | " | H | CH₃CHCH₃ | 16 | 8 | " | 20 | ether/n-hexane | 95 | |
| 44 | " | " | H | —CH₂C₆H₅ | 15 | 8 | " | 17 | ether | 85 | |
| 45 | " | " | H | C₆H₅ | 16 | 8 | " | 21 | ether/n-hexane | 86 | |
| 46 | " | " | H | p-Cl—C₆H₄ | 16 | 8 | " | 21 | ether/n-hexane | 94 | |
| 47 | " | " | H | p-CH₃O—C₆H₄ | 16 | 8 | " | 21 | ether/n-hexane | 91 | |
| 48 | " | " | H | morpholinoethyl¹ | 14 | 8 | " | 17 | water | 87 | |
| 49 | Cl | H | CH₃ | CH₃ | 16 | 8 | " | 17 | acetone/hexane | 97 | |
| 50 | Cl | H | C₂H₅ | C₂H₅ | 14 | 8 | " | 17 | acetone/hexane | 91 | |
| 51 | H | Cl | CH₃ | CH₃ | 24 | 12 | " | 17 | ethylacetate/ether | 94 | |
| 52 | H | Cl | C₂H₅ | C₂H₅ | 16 | 8 | " | 17 | ethylacetate/ether | 87 | |
| 53 | Br | H | CH₃ | CH₃ | 14 | 7 | " | 17 | acetone/hexane | 93 | |

TABLE 3-continued

| Compd | Substituent | | | | Reaction Conditions | | | | Solvent for | Yield | |
|---|---|---|---|---|---|---|---|---|---|---|---|
| Ib | X | X' | $R_1$ | $R_2$ | 15% $K_2CO_3$ (ml) | THF (ml) | Temp °C. | Time (hr) | Recrystallization | % | Note |
| 54 | Br | H | $C_2H_5$ | $C_2H_5$ | 14 | 7 | " | 17 | ethylacetate/ether | 99 | |

[1] as hydrochloride
[2] r.t.: room temperature

TABLE 4

| Compd. Ib | m.p. °C. | Molecular Formula (M.W.) | Elementary Analysis (%) | | | | NMR δ ppm (J Hz) |
|---|---|---|---|---|---|---|---|
| | | | C | H | N | S Cl | |
| 29 | 209 | $C_9H_7NO_5Cl_2S$·½$H_2O$ (316.631) | 34.14 / 34.22 | 2.39 / 2.44 | 4.42 / 4.51 | 10.13 / 10.02    22.39 / 22.81 | ($d_6$-acetone): 3.27~4.05 (2H, m), 5.55 (1H, dd, J = 10.2 & 6.6), 6.4 (1H, b), 6.67 (2H, bs), 7.90 (1H, t, J = 1.2) |
| 30 | 235~236 | $C_{18}H_{14}NSCl_2O_5K$·$H_2O$ (424.348) | 36.79 / 36.64 | 3.80 / 3.81 | 3.30 / 3.29 | 7.56 / 7.89    16.70 / 16.92 | ($d_6$-DMSO): 1.03 (6H, t, J = 7.0), 3.26 (4H, q, J = 7.0), 3.00~3.70 (2H, m), 4.95 (1H, dd, J = 10 & 7.0), 7.71 (1H, t, J = 1.0) |
| 31 | 120~121 | $C_{15}H_{19}NSCl_2O_5$ (396.292) | 45.46 / 45.36 | 4.83 / 4.80 | 3.53 / 3.25 | 8.09 / 8.12    17.89 / 17.83 | ($d_6$-acetone): 0.80 (6H, t, J = 7.0), 1.00~1.80 (4H, m), 3.26 (4H, t, J = 7.0), 3.25~4.20 (2H, m), 5.57 (1H, dd, J = 10 & 7.0), 7.94 (1H, t, J = 1.0), 8.93 (1H, b) |
| 32 | 176~177 | $C_{15}H_{19}NSCl_2O_5$ (396.292) | 45.46 / 45.23 | 4.83 / 4.75 | 3.53 / 3.48 | 8.09 / 7.91    17.89 / 17.95 | ($d_6$-acetone): 127 (12H, d, J = 7.0), 3.40~4.10 (4H, m), 5.57 (1H, dd, J = 10 & 7.0), 8.00 (1H, t, J = 1.0) |
| 33 | 92~93 | $C_{14}H_{17}NSCl_2O_5$ (382.265) | 43.99 / 43.85 | 4.48 / 4.35 | 3.66 / 3.77 | 8.39 / 8.33    18.55 / 18.43 | ($d_6$-acetone): 0.87 (3H, t, J = 7.0), 1.05~1.80 (4H, m), 2.85 (3H, s), 3.25 (2H, t, J = 7.0), 3.40~4.10 (2H, m), 5.60 (1H, dd, J = 10 & 7.0), 7.93 (1H, t, J = 1.0), 8.00~9.80 (1H, b) |
| 34 | 127~128 | $C_{28}H_{19}NSCl_2O_5$ (492.381) | 56.11 / 56.01 | 3.89 / 3.81 | 2.84 / 2.83 | 6.51 / 6.31    14.40 / 14.62 | ($d_6$-acetone): 3.30~4.05 (2H, m), 4.44 (4H, s), 5.55 (1H, dd, J = 10 & 7.0), 7.00~7.35 (10H, m), 7.85 (1H, t, J = 1.0), 7.30~8.50 (1H, b) |
| 35 | 148~149 | $C_{17}H_{15}NSCl_2O_5$ (416.284) | 49.05 / 48.90 | 3.63 / 3.72 | 3.36 / 3.42 | 7.70 / 7.56    17.03 / 17.20 | ($d_6$-acetone): 2.73 (3H, s), 3.30~4.05 (2H, m), 4.43 (2H, s), 5.57 (1H, dd, J = 10 & 7.0), 7.32 (5H, s), 7.95 (1H, t, J = 1.0), 9.37 (1H, b) |
| 36 | 194~195 | $C_{16}H_{12}NSCl_2O_5K$·$H_2O$ (458.365) | 41.93 / 41.73 | 3.08 / 3.14 | 3.05 / 3.30 | 6.99 / 7.06    15.46 / 15.75 | ($d_6$-DMSO): 3.00~3.70 (4H, m), 3.28 (3H, s), 4.96 (1H, dd, J = 10 & 7.0), 710~7.50 (5H, m), 7.62 (1H, t J = 1.0) |
| 37 | 148~149 | $C_{16}H_{19}NSCl_2O_5$ (408.303) | 47.07 / 47.34 | 4.69 / 4.73 | 3.43 / 3.41 | 7.85 / 7.50    17.37 / 17.12 | ($d_6$-acetone): 0.70~1.90 (10H, m), 2.80 (3H, s), 3.00~4.10 (3H, m), 5.51 (1H, dd, J = 10 & 7.0), 6.10 (1H, b), 7.91 (1H, s) |
| 38 | 181~182 | $C_{18}H_{18}NSCl_2O_5$ (366.223) | 42.64 / 42.44 | 3.58 / 3.59 | 3.82 / 3.77 | 8.76 / 8.56    19.36 / 19.20 | ($d_6$-acetone): 1.65~2.15 (4H, m), 3.10~3.60 (4H, m), 3.30~4.25 (2H, m), 5.56 (1H, dd, J = 10 & 7.0), 7.90 (1H, t, J = 1.0), 8.86 (1H, b) |
| 39 | 199~200 | $C_{14}H_{15}NSCl_2O_5$ (380.25) | 44.22 / 44.17 | 3.98 / 3.95 | 3.68 / 3.71 | 8.43 / 8.23    18.65 / 18.57 | ($d_6$-DMSO): 1.50 (6H, b), 3.15 (4H, b), 3.10~3.85 (2H, m), 5.05 (1H, dd, J = 10 &7.0), 7.76 (1H, t, J = 1.0) |
| 40 | 228~229 | $C_{18}H_{18}NSCl_2O_6$ (382.222) | 40.85 / 40.43 | 3.43 / 3.39 | 3.66 / 3.60 | 8.39 / 8.28    18.55 / 18.37 | ($d_6$-DMSO): 2.80~3.40 (4H, m), 3.40~4.10 (6H, m), 5.52 (1H, dd, J = 10 & 7.0), 7.83 (1H, t, J = 1.0) |
| 41 | 215~216 | $C_{10}H_9NSCl_2O_5$ (326.157) | 36.83 / 36.93 | 2.78 / 3.04 | 4.29 / 4.17 | 9.83 / 9.51    21.74 / 21.09 | ($d_6$-acetone): 2.57 (3H, d, J = 5.0), 3.35~4.20 (2H, m), 5.57 (1H, dd, J = 10 & 7.0), 6.50 (1H, q, J = 5.0), 7.92 (1H, t, J = 1.0), 7.90~8.95 (1H, b) |
| 42 | 200~201 | $C_{12}H_{18}NSCl_2O_5$ (354.212) | 40.69 / 40.52 | 3.70 / 3.73 | 3.95 / 3.91 | 9.05 / 8.82    20.02 / 19.96 | ($d_6$-acetone): 0.83 (3H, t, J = 7.0), 1.25~1.70 (2H, m), 2.86 (2H, q, J = 7.0), 3.30~4.05 (2H, m), 5.55 (1H, dd, J = 10 & 7.0), 6.85 (1H, bt), 7.90 (1H, t, J = 1.0) |
| 43 | 184~185 | $C_{14}H_{17}NSCl_2O_5$ (354.212) | 40.69 / 40.53 | 3.70 / 3.68 | 3.95 / 4.00 | 9.05 / 8.89    20.02 / 19.72 | ($d_6$-acetone): 1.06 (6H, d, J = 7.0), 3.20~4.10 (3H, m), 5.60 (1H, dd, J = 10 & 7.0), 6.52 (1H, bd, J = 7.0), 7.95 (1H, t, J = 1.0), 9.25~10.05 (1H, b) |
| 44 | 199~200 | $C_{16}H_{13}NSCl_2O_5$ (402.256) | 47.78 / 47.90 | 3.26 / 3.47 | 3.48 / 3.40 | 7.97 / 7.59    17.63 / 17.68 | ($d_6$-acetone): 3.25~4.10 (2H, m), 4.15 (2H, d, J = 6.0), 5.52 (1H, dd, J = 10 & 7.0), 7.17 (5H, s), 7.75 (1H, t, J = 1.0), 7.30~9.10 (1H, b) |
| 45 | 201~202 | $C_{15}H_{11}NSCl_2O_5$ (388.229) | 46.41 / 46.31 | 2.86 / 2.92 | 3.61 / 3.61 | 8.26 / 8.06    18.26 / 17.96 | ($d_6$-acetone): 3.30~4.00 (2H, m), 5.51 (1H, dd, J = 10 & 7.0), 6.85~7.35 (5H, m), 7.93 (1H, t, J = 1.0), 8.60 (1H, b), 9.20 (1H, bs) |
| 46 | 189~190 | $C_{15}H_{10}NSCl_8O_5$ | 42.63 | 2.38 | 3.31 | 7.59    25.16 | ($d_6$-acetone): 3.35~4.10 (2H, m), 5.56 |

TABLE 4-continued

| Compd. Ib | m.p. °C. | Molecular Formula (M.W.) | Elementary Analysis (%) C | H | N | S | | NMR δ ppm (J Hz) |
|---|---|---|---|---|---|---|---|---|
| | | (422.670) | 42.93 | 2.71 | 3.20 | 7.42 | 24.55 | (1H, dd, J = 10 & 7.0), 7.27 (4H, s), |
| | | | | | | | | 7.93 (1H, t, J = 1.0), 7.50~9.30 (1H, b), |
| | | | | | | | | 9.40 (1H, b) |
| 47 | 173~174 | $C_{16}H_{18}NSCl_2O_6$· | 45.95 | 3.13 | 3.35 | 7.67 | 16.95 | (d6-acetone): 3.30~4.20 (2H, m), 3.67 |
| | | (418.255) | 45.99 | 3.23 | 3.34 | 7.52 | 16.74 | (3H, s), 5.53 (1H, dd, J = 10 & 7.0), |
| | | | | | | | | 6.77, 7.15 (4H, ABq, J = 9.0), 7.82 (1H, |
| | | | | | | | | t, J = 1.0), 8.75 (1H, b), 8.92 (1H, bs) |
| 48 | 250~251 | $C_{15}H_{13}N_2SCl_2O_6$·HCl | 39.01 | 4.15 | 6.07 | 6.94 | | (d6-DMSO): 2.80~3.40 (8H, m), 340~ |
| | | (461.75) | 38.96 | 4.17 | 6.06 | 7.07 | | 4.10 (6H, m), 5.53 (1H, dd, J = 10 & 7.0), |
| | | | | | | | | 7.86 (1H, t, J = 1.0), 8.10 (1H, t, J = 5.0) |
| 49 | 164~166 | $C_{11}H_{12}NO_5ClS$ | 43.21 | 3.96 | 4.58 | 10.49 | 11.60 | (d6-acetone): 2.70 (6H, s), 3.58 (1H, dd, |
| | | (305.736) | 43.01 | 4.00 | 4.57 | 10.21 | 11.51 | J = 16.8 & 6.9), 3.90 (1H, dd, J = 16.8 & |
| | | | | | | | | 10.2), 5.56 (1H, dd, J = 10.2 & 6.9), 7.63 |
| | | | | | | | | (2H, s), 7.6~9.3 (1H, b) |
| 50 | 164~165 | $C_{18}H_{16}NO_5ClS$ | 46.78 | 4.83 | 4.20 | 9.60 | 10.62 | (d6-acetone): 1.11 (6H, t, J = 7.0), 3.23 |
| | | (333.790) | 46.59 | 4.85 | 4.21 | 9.34 | 10.30 | (4H, q, J = 7.0), 3.55 (1H, dd, J = 16.5 & |
| | | | | | | | | 6.8), 3.89 (1H, dd, J = 16.5 & 10.5), 5.53 |
| | | | | | | | | (1H, dd, J = 10.5 & 6.8), 7.66 (2H, s) |
| 51 | 145 | $C_{11}H_{12}NO_5ClS$ | 43.21 | 3.96 | 4.58 | 10.49 | 11.60 | (d6-acetone): 2.80 (6H, s), 3.25~3.93 |
| | | (305.733) | 42.85 | 4.02 | 4.59 | 10.30 | 11.75 | (2H, m), 5.43 (1H, dd, J = 10.2 & 6.8), |
| | | | | | | | | 7.03 (1H, s), 7.88 (1H, t, J = 1.2) |
| 52 | 83~85 | $C_{18}H_{16}NClO_5S$·¾ $H_2O$ | 44.96 | 5.08 | 4.03 | 9.23 | 10.21 | (d6-acetone): 1.08 (6H, t, J = 7.2), 3.20~ |
| | | (347.305) | 44.92 | 4.93 | 4.32 | 9.49 | 10.17 | 3.90 (6H, m), 5.43 (1H, dd, J = 10.5 & |
| | | | | | | | | 7.0), 7.00 (1H, s), 7.91 (1H, t, J = 1.2), |
| | | | | | | | | 4.2~5.3 (b) |
| | | | | | | | Br | |
| 53 | 194~195 | $C_{11}H_{12}NO_5BrS$ | 37.73 | 3.45 | 4.00 | 9.16 | 22.82 | (d6-acetone): 2.70 (6H, s), 3.60 (1H, |
| | | (350.192) | 37.73 | 3.57 | 3.87 | 9.20 | 22.97 | dd, J = 16.6 & 7.0), 3.93 (1H, dd, J = |
| | | | | | | | | 16.6 & 10.5), 5.54 (1H, dd, J = 10.5 & |
| | | | | | | | | 7.0), 7.66 (1H, m), 7.75 (1H, m), |
| | | | | | | | | 7.2~8.5 (1H, b) |
| 54 | 161~162 | $C_{18}H_{16}NO_5BrS$ | 41.28 | 4.26 | 3.70 | 8.48 | 21.13 | (d6-acetone): 1.10 (6H, t, J = 7.1), 3.23 |
| | | (378.246) | 41.26 | 4.37 | 3.78 | 8.35 | 20.42 | (4H, q, J = 7.1), 3.57 (1H, dd, J = 16.5 |
| | | | | | | | | & 6.8), 3.90 (1H, dd, J = 16.5 & 10.5), |
| | | | | | | | | 5.52 (1H, dd, J = 10.5 & 6.8), 7.70 (1H, |
| | | | | | | | | m), 7.79 (1H, m), 7.2~8.5 (1H, b) |

EXAMPLE 55

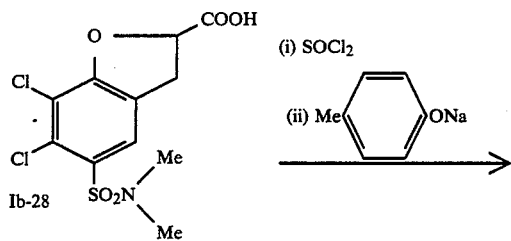

To a mixed solution of 10 ml of benzene with 1.5 ml (21.5 mmol) of thionyl chloride is added 1 g (2.94 mmol) of 5-(N,N-dimethylsulfamoyl)-6,7-dichlorobenzofuran-2-carboxylic acid (I b-28) and the mixture refluxed for 40 minutes under heating. The reaction mixture is evaporated to dryness under reduced pressure to leave an residual oil, to which 10 ml of benzene is then added. Sodium p-cresol (500 mg) is added thereto under cooling and the mixture is allowed to stand for 20 minutes. The mixture is evaporated under reduced pressure to leave a residue, which is extracted with ethyl acetate/water. The ethyl acetate layer is washed with a saturated solution of aqueous sodium hydrogencarbonate, filtered in order to remove insoluble matters, dried over sodium sulfate, and evaporated to give a crystalline residue, which is then washed with ether and collected by filtration to finally give 1.028 g of p-tolyl 5-(N,N-dimethylsulfamoyl)-6,7-dichlorobenzofuran-2-carboxylate (I c-55), yield 82%, m.p. 176°-177° C.

Analysis Calcd (%) for $C_{18}H_{17}NSCl_2O_5$: C, 50.24; H, 3.98; N, 3.26; S, 7.45; Cl, 16.48. Found (%): C, 50.25; H, 4.04; N, 3.21; S, 7.14; Cl, 16.24.

NMR (CDCl$_3$) δppm: 2.33 (s, 3H), 2.87 (s, 6H), 3.25-4.00 (m, 2H), 5.58 (dd, 1H, J=10 and 7.0), 9.67 and 7.20 (d each, 4H, J=1.0).

EXAMPLE 56

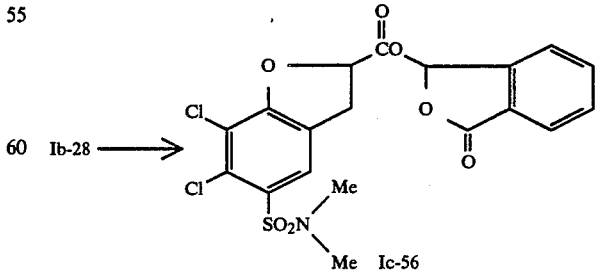

To a solution of 1 g (2.94 mmol) of the compound (I b-28) dissolved in 10 ml of acetonitrile is added 425 mg (2.94×2.1 mmol) of potassium carbonate and the mixture is stirred for one hour at room temperature. After the confirmation by TLC [silica gel; dichloromethane/ethanol (10:1)/1% acetic acid] that no free acid is left, the precipitated crystals (1.35 g) are collected by filtration. The crystals are added to 20 ml of acetonitrile and cooled to −20° C. To the mixture is added 1.32 g (2.94×2.1 mmol) of 1-phthalidyl bromide (=1,3-dihydro-3-oxyisobenzofuran-1-yl) and then stirred at room temperature. Dimethylformamide (6 ml) is added thereto, and the resulting mixture is refluxed under heating for 30 minutes. After removal of insoluble matters by filtration, the reaction mixture is condensed under reduced pressure to leave a residue, which is then extracted with ethyl acetate. The organic layer is washed with water, dried over magnesium sulfate, and evaporated to dryness under reduced pressure. The resulting residue is chromatographed on silica gel with dichloromethane as an eluent to give 770 mg of the objective 1-phthalidyl 5-(N,N-dimethylsulfamoyl)-6,7-dichloro-2,3-dihydrobenzofuran-2-carboxylate (I c-56), yield 56%, m.p. 152°–154° C.

Analysis Calcd (%) for $C_{19}H_{15}NSCl_2O_7 \cdot \frac{1}{2}H_2O$: C, 47.71; H, 3.45; N, 2.92; S, 6.70; Cl, 14.82. Found (%): C, 47.88; H, 3.26; N, 2.99; S, 6.50; Cl, 14.61.

NMR ($d_6$-acetone) δppm: 2.83 (s, 6H), 3.15–4.15 (m, 2H), 5.60–5.90 (m, 1H), 7.54 (s, 1H), 7.60–8.00 (m, 5H)

EXAMPLE 57

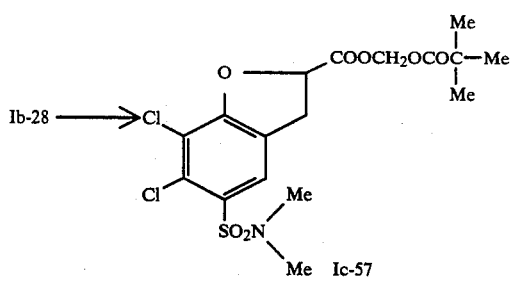

To a solution of potassium salt of the compound (I b-28) (1 g, 2.94 mmol) dissolved in 10 ml of acetonitrile is dropwise added 1.5 g (2.94×2.1 mmol) of pivaloyloxymethyl iodide at 20° C., and the mixture is refluxed for 2.5 hours while being stirred under heating. The insoluble matters are filtered off and the reaction solution is extracted with ethylacetate. The organic layer is washed with water, dried over magnesium sulfate, and evaporated to dryness under reduced pressure to give a crystalline residue, which is chromatographed on silica gel column with dichloromethane as an eluent to give 911 mg of the objective pivaloyloxymethyl 5-(N,N-dimethylsulfamoyl)-6,7-dichloro-2,3-dihydrobenzofuran-2-carboxylate (I c-57), yield 69%, m.p. 113°–114° C.

Analysis Calcd (%) for $C_{17}H_{21}NSCl_2O_7$: C, 44.94; H, 4.66; N, 3.08; S, 7.06; Cl, 15.61. Found (%): C, 44.93; H, 4.65; N, 3.14; S, 6.98; Cl, 15.73.

NMR ($d_6$-acetone) δppm: 1.16 (s, 9H), 2.84 (s, 6H), 3.10–4.10 (m, 2H), 5.62 (dd, 1H, J=10 and 7.0), 5.84 (s, 2H), 7.88 (t, 1H, J=1.0).

EXAMPLE 58

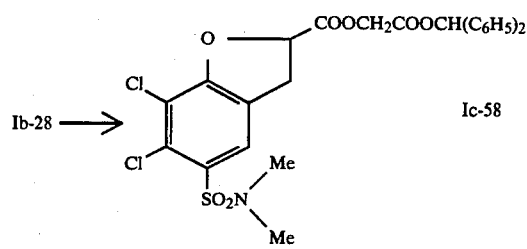

With 1.5 ml of thionyl chloride is treated 1 g of the compound (I b-28) in 5 ml of benzene to form the corresponding acid chloride, whose solution dissolved in 8 ml of benzene is dropwise added at 0° C. to a solution of benzhydryl glycolate (855 mg), triethylamine (300 mg), and 4-dimethylaminopyridine (35 mg) in 5 ml of benzene. The mixture is stirred for 1 hour under ice-cooling and then extracted with dichloromethane. The organic layer is washed with water, dried over magnesium sulfate, and evaporated to dryness under reduced pressure to give a residue, which is chromatographed on silica gel column with dichloromethane as an eluent to give 1.35 g of the objective diphenylmethyloxycarbonylmethyl 5-(N,N-dimethylsulfamoyl)-6,7-dichloro-2,3-dihydrobenzofuran-2-carboxylate (I c-58), yield 81%, m.p. 56°–58° C.

Analysis Calcd (%) for $C_{26}H_{23}NSCl_2O_7$: C, 55.33; H, 4.11; N, 2.48; S, 5.68; Cl, 12.56. Found (%): C, 55.82; H, 4.22; N, 2.60; S, 5.51; Cl, 12.29.

NMR (CDCl$_3$) δppm: 8.82 (s, 6H), 3.10–3.90 (m, 2H), 4.67 and 4.92 (d each, 2H, J=16), 5.43 (dd, 1H, J=10 and 6.3), 6.87 (s, 1H), 7.27 (s, 10H), 7.75 (t, 1H, J=1.0).

EXAMPLE 59

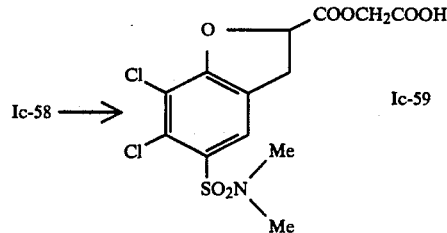

To a solution of 850 mg of the compound (I c-58) prepared in Example 58 dissolved in 1 ml of anisole is added 1 ml of trifluoroacetic acid while being stirred under ice-cooling. After one hour reflux at room temperature, the reaction mixture is evaporated to dryness under reduced pressure. The residue is recrystallized from ether/n-hexane to give 599 mg of the objective 5-(N,N-dimethylsulfamoyl)-6,7-dichloro-2,3-dihydrobenzofuran-2-ylcarbonyloxyacetic acid (I c-59), yield 100%, m.p. 149°–150° C.

Analysis Calcd (%) for $C_{13}H_{13}NSCl_2O_7$: C, 39.21; H, 3.29; N, 3.52; S, 8.05; Cl, 17.81. Found (%): C, 39.16; H, 3.42; N, 3.60; S, 7.98; Cl, 17.65.

NMR ($d_6$-acetone) δppm: 2.85 (s, 6H), 3.30–4.15 (m, 2H), 4.67 and 4.87 (ABd, 2H, J=16), 5.67 (dd, 1H, J=10 and 6.3), 7.88 (t, 1H, J=1.0).

EXAMPLES 60 TO 61

In the same manner as in aforementioned Examples 58 and 59, 5-(N,N-diethylsulfamoyl)-6,7-dichlorobenzofuran-2-carboxylic acid (I b-30; employed as the free acid) is converted to the respective compounds as follows.

Diphenylmethyloxycarbonylmethyl 5-(N,N-diethylsulfamoyl)-6,7-dichloro-2,3-dihydrobenzofuran-2-carboxylate (I c-60):

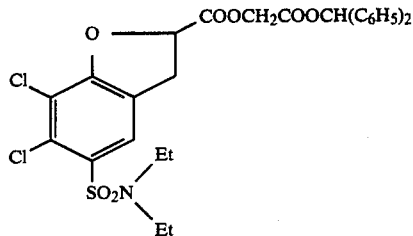

m.p. 49°-50° C.

Analysis Calcd (%) for $C_{28}H_{27}NSCl_2O_7$: C, 56.76; H, 4.59; N, 2.36; S, 5.41; Cl, 11.97. Found (%): C, 56.69; H, 4.64; N, 2.47; S, 5.26; Cl, 12.26.

NMR (CDCl$_3$) δppm: 1.12 (t, 6H, J=7.0), 3.32 (q, 4H, J=7.0), 3.20-3.80 (m, 2H), 4.70 and 4.93 (ABd, 2H, J=17), 5.44 (dd, 1H, J=10 and 7.0), 6.90 (s, 1H), 7.24 (s, 10H), 7.82 (t, 1H, J=1.0).

5-(N,N-Diethylsulfamoyl)-6,7-dichloro-2,3-dihydrobenzofuran-2-ylcarbonyloxy acetic acid (I c-61):

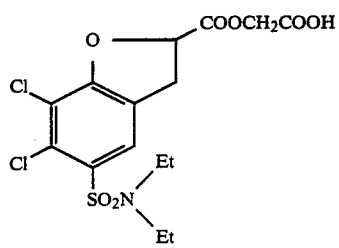

m.p. 102°-103° C.

Analysis Calcd (%) for $C_{15}H_{17}NSCl_2O_7$: C, 42.27; H, 4.02; N, 3.29; S, 7.52; Cl, 16.63. Found (%): C, 42.03; H, 4.04; N, 3.32; S, 7.45; Cl, 16.80.

NMR (d$_6$-acetone) δppm: 1.10 (t, 6H, J=7.0), 3.35 (q, 4H, J=7.0), 3.40-4.20 (m, 2H), 4.76 (d, 2H, J=1.0), 5.68 (dd, 1H, J=10 and 7.0), 7.93 (t, 1H, J=1.0).

EXAMPLE 62

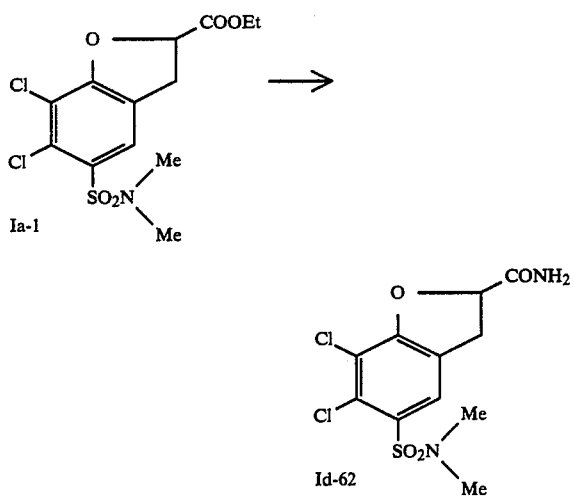

A mixture of 500 mg (1.358 mmol) of ethyl 5-(N,N-dimethylsulfamoyl)-6,7-dichlorobenzofuran-2-carboxylate (I a-1) with 50 1 ml of 20% ammonia/methanol solution is stirred for 17 hours at room temperature. The reaction mixture is evaporated to dryness under reduced pressure to give a crystalline residue, which is suspended in ether and then collected by filtration to give finally 448 mg of 5-(N,N-dimethylsulfamoyl)-6,7-dichloro-2,3-dihydrobenzofuran-2-carbonamide (I d-62), yield 97%, m.p. 209°-210° C.

Analysis Calcd (%) for $C_{11}H_{12}NSCl_2O_4$: C, 38.95; H, 3.57; N, 8.26; S, 9.45; Cl, 20.90. Found (%): C, 38.70; H, 3.62; N, 8.22; S, 9.52; Cl, 21.16.

NMR (d$_6$-acetone) δppm: 2.86 (s, 6H), 3.25-3.96 (m, 2H), 5.45 (dd, 1H, J=10 and 7.0), 6.50-7.50 (b, 2H), 7.90 (t, 1H, J=1.0).

Under the same conditions as mentione above, the compound (I a-1) is reacted with methylamine and dimethylamine to give the following compounds, respectively.

5-(N,N-Dimethylsulfamoyl)-N'-methyl-6,7-dichloro-2,3-dihydrobenzofuran-2-carbonamide (I d-63):

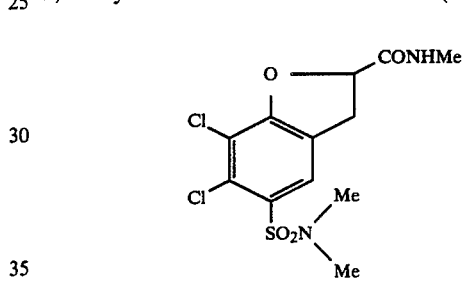

m.p. 182°-184° C.

Analysis Calcd (%) for $C_{12}H_{14}NSCl_2O_4$: C, 40.80; H, 4.00; N, 7.93; S, 9.08; Cl, 20.07. Found (%): C, 40.59; H, 4.01; N, 7.91; S, 8.96; Cl, 20.03.

NMR (CDCl$_3$) δppm: 2.85 (s, 6H), 2.87 (d, 3H, J=7.0), 3.30-4.00 (m, 2H), 5.35 (dd, 1H, J=10 and 7.0), 6.60 (b, 1H), 7.84 (t, 1H, J=1.0).

5-(N,N-Dimethylsulfamoyl)-N',N'-dimethyl-6,7-dichloro-2,3-dihydrobenzofuran-2-carbonamide (I d-64):

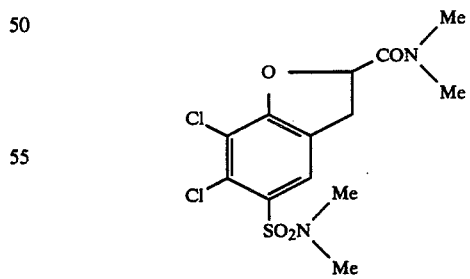

m.p. 171°-172 C.

Analysis Calcd (%) for $C_{13}H_{16}NSCl_2O_4\cdot\frac{1}{4}H_2O$: C, 41.95; H, 4.28; N, 7.54; S, 8.63. Found (%): C, 42.26; H, 4.48; N, 7.53; S, 8.62.

NMR (CDCl$_3$) δppm: 2.78 (s, 6H), 3.05 (s, 3H), 3.25 (s, 3H), 3.20-4.15 (m, 2H), 5.67 (dd, 1H, J=10 and 7.0), 7.77 (t, 1H, J=1.0).

EXAMPLE 65

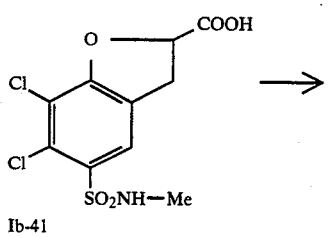

To a solution of 1.5 g of 5-(N-methylsulfamoyl)-6,7-dichloro-2,3-dihydrobenzofuran-2-carboxylic acid (I b-41) dissolved in 20 ml of dichloromethane is gently added 1.3 g of diphenyldiazomethane at 4° C. The mixture is stirred for 2 hours at room temperature, the remaining reagent in which is decomposed by the addition of 10% hydrochloric acid. The mixture is combined with 60 ml of dichloromethane, then washed with water, dried over magnesium sulfate, and evaporated to dryness under reduced pressure to give an oily residue, which is chromatographed on 30 g of silica gel. Fractions eluated with dichloromethane is treated with ether/hexane to give 2.06 g (yield 91%) of the objective ester compound, i.e., benzhydryl 5-(N-methylsulfamoyl)-6,7-dichloro-2,3-dihydrobenzofuran-2-carboxylate, m.p. 132°–133° C.

To a solution of 1.655 g of the ester compound dissolved in 20 ml of dimethylformamide is gently added 180 mg of sodium hydride (50% suspension) at 4° C. and the mixture is stirred for 1 hour at room temperature. After dropwise addition of 401 mg of ethyl chloroform (ClCOOEt), the reaction mixture is poured into water and extracted with 300 ml of ether. The organic layer is dried over magnesium sulfate, evaporated to dryness under reduced pressure to give an oily residue, which is chromatographed on 100 g of silica gel with dichloromethane as an eluent. The fractions are collected and treated with n-hexane to give 1.314 g (yield 69%) of the objective urethane compound, i.e., benzhydryl 5-(N-methyl-N-ethoxycarbonylsulfamoyl)-6,7-dichloro-2,3-dihydrobenzofuran-2-carboxylate, m.p. 111°–112° C.

Analysis Calcd (%) for $C_{26}H_{23}NO_7Cl_2S$: C, 55.33; H, 4.11; N, 2.48; S, 5.68; Cl, 12.56. Found (%): C, 55.50; H, 4.17; N, 2.43; S, 5.61; Cl, 12.54.

NMR (CDCl$_3$) δppm: 1.07 (t, 3H, J=7.0), 3.20–3.90 (m, 2H), 3.42 (s, 3H), 4.05 (q, 2H, J=7.0), 5.48 (dd, 1H, J=10 and 7.0), 6.93 (s, 1H), 7.30 (s, 5H), 7.36 (s, 5H), 7.96 (t, 1H, J=1.0).

To a solution of 1.314 g of the urethane compound dissolved in 3 ml of anisole is dropwise added 2.5 ml of trifluoroacetic acid while being cooled at 4° C. and then the mixture is stirred at room temperature for 1 hour. The reaction mixture is evaporated to dryness under reduced pressure to give a residue, which is treated with n-hexane to give 943 mg of the objective 5-(N-methyl-N-ethoxycarbonylsulfamoyl)-6,7-dichloro-2,3-dihydrobenzofuran-2-carboxylic acid (I e-65), yielded quantitatively. This is recrystallized from acetone/ether/n-hexane to give crystals, m.p. 199°–201° C.

Analysis Calcd (%) for $C_{13}H_{13}NO_7Cl_2S$: C, 39.21; H, 3.29; N, 3.52; S, 8.05; Cl, 17.81. Found (%): C, 39.40; H, 3.43; N, 3.54; S, 7.92; Cl, 17.66.

NMR (d$_6$-acetone) δppm: 1.07 (t, 3H, J=7.0), 3.40 (s, 3H), 3.40–4.05 (m, 2H), 4.05 (q, 2H, J=7.0), 5.62 (dd, 1H, J=10 and 7.0), 8.03 (t, 1H, J=1.0), 9.30–10.20 (b, 1H).

EXAMPLES 66–67

To a solution of 1.0 g of ethyl 5-(N-methylsulfamoyl)-2,3-dihydrobenzofuran-2-carboxylate (I a-14) dissolved in 10 ml of anhydrous dimethylformamide is added 149 mg of 50% sodium hydride and then stirred for 30 minutes. After addition of 396 mg of ethyl bromide under ice-cooling, the mixture is stirred for 30 minutes under ice-cooling and successively for another 30 minutes at room temperature. 1.0 ml Of 10% hydrochloric acid and then 10 ml of water are added to the reaction mixture, which is then extracted with 80 ml of ether. The ether layer is dried over magnesium sulfate, evaporated to dryness under reduced pressure to give a residue. A solution of the residue dissolved in ether is combined with a ether solution of diazoethane and allowed to react for 30 minutes. The reaction mixture is evaporated to dryness under reduced pressure to give a residue, which is chromatographed on silica gel with ether/dichloromethane as an eluent. The fractions are collected and treated with n-hexane to give 905 mg of the objective crystalline product, i.e., ethyl 5-(N-ethyl-N-methylsulfamoyl)-6,7-dichloro-2,3-dihydrobenzofuran-2-carboxylate (I f-66), yield 84%, m.p. 80°–81° C.

Analysis Calcd (%) for $C_{14}H_{17}NCl_2O_5S$: C, 43.99; H, 4.48; N, 3.66; S, 8.39; Cl, 18.55. Found (%): C, 43.77; H, 4.47; N, 3.84; S, 8.41; Cl, 18.71.

NMR (CDCl$_3$) δppm: 1.16 (t, 3H, J=7.0), 1.30 (t, 3H, J=7.0), 2.86 (s, 3H), 3.27 (q, 2H, J=7.0), 3.20–3.90 (m, 2H), 4.28 (q, 2H, J=7.0), 6.22 (dd, 1H, J=10 and 7.0), 7.87 (t, 1H, J=1.0).

In the same reaction conditions as in mentioned above, the compound (I a-14) is reacted with propyl bromide to give the following compound.

Ethyl 5-(N-methyl-N-propylsulfamoyl)-6,7-dichloro-2,3-dihydrobenzofuran-2-carboxylate (I f-67): m.p. 70°–71° C.

Analysis Calcd (%) for C₁₅H₁₉NCl₂O₅S: C, 45.46; H, 4.83; N, 3.53; S, 8.09; Cl, 17.89. Found (%): C, 45.41; H, 4.75; N, 3.63; S, 8.10; Cl, 18.10.

NMR (CDCl₃) δppm: 0.87 (t, 3H, J=7.0), 1.30 (t, 3H, J=7.0), 1.30–1.90 (m, 2H), 2.84 (s, 3H), 3.19 (t, 2H, J=7.0), 3.20–3.85 (m, 2H), 4.27 (q, 2H, J=7.0), 5.37 (dd, 1H, J=10 and 7.0), 7.87 (t, 1H, J=1.0).

EXAMPLES 68–69

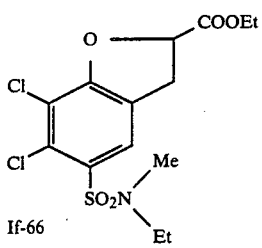

If-66

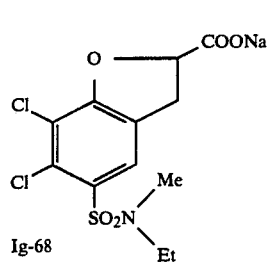

Ig-68

To a solution of 600 mg of ethyl 5-(N-ethyl-N-methylsulfamoyl)-6,7-dichloro-2,3-dihydrobenzofuran-2-carboxylate (I f-66) dissolved in 2 ml of acetonitrile is added 1.65 ml of 1N sodium hydroxide and the mixture stirred for 30 minutes. The reaction mixture is evaporated to dryness under reduced pressure to give a residue, which is made acid by the addition of 10% hydrochloric acid and extracted with 50 ml of ethyl acetate. The ethyl acetate layer is dried over magnesium sulfate and evaporated to give a viscous residue. The residue is dissolved in 10 ml of acetonitrile, then combined with 1.6 ml of 1N sodium hydroxide, and the mixture is stirred for 30 under ice-cooling. The precipitating crystals are collected by filtration. Sodium 5-(N-Ethyl-N-methylsulfamoyl)-6,7-dichloro-2,3-dihydrobenzofuran-2-carboxylate (I g-68) (591 mg). This is recrystallized from water/ethanol to give an authentic specimen, yield 91%, m.p. 176°–177° C.

Analysis Calcd (%) for C₁₂H₁₂NCl₂O₅S H₂O: C, 36.56; H, 3.58; N, 3.55; S, 8.13. Found (%): C, 36.58; H, 3.47; N, 3.41; S, 8.37.

NMR (d₆-DMSO) δppm: 1.06 (t, 3H, J=7.0), 2.80 (s, 3H), 3.20 (q, 2H, J=7.0), 3.20–3.75 (m, 2H), 3.36 (s), 5.06 (dd, 1H, J=11 and 7.0), 7.76 (t, 1H, J=1.0).

In the same reaction conditions as in mentioned above, the compound (I f-67) is hydrolyzed to give the following compound.

Sodium 5-(N-methyl-N-propylsulfamoyl)-6,7-dichloro-2,3-dihydrobenzofuran-2-carboxylate (I g-69): m.p. 162°–163° C.

Analysis Calcd (%) for C₁₃H₁₄NCl₂NaO₅S2H₂O: C, 36.63; H, 4.26; N, 3.29; Cl, 16.63; S, 7.52. Found (%): C, 36.70; H, 4.15; N, 3.28; Cl, 16.76; S, 7.74.

NMR (d₆-DMSO) δppm: 0.80 (t, 3H, J=7.0), 1.25–1.80 (m, 2H), 2.77 (s, 3H), 3.12 (t, 2H, J=7.0), 3.32 (s), 3.10–3.75 (m, 2H), 5.04 (dd, 1H, J=10 and 7.0), 7.74 (t, 1H, J=1.0).

EXAMPLE 70

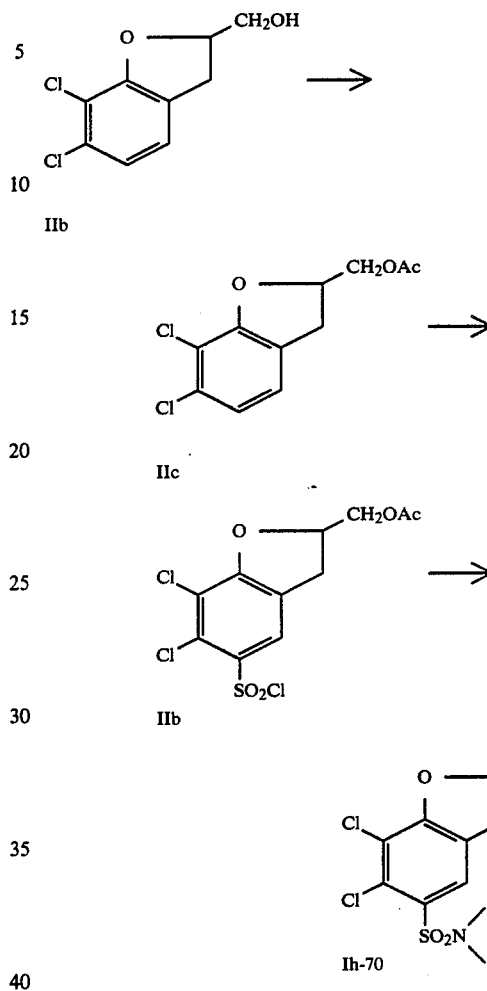

To a solution of 10 g (45.65 mmol) of 2-hydroxymethyl-6,7-dichloro-2,3-dihydrobenzofuran and 11.13 g (45.65×2 mmol) of 4-dimethylaminopyridine dissolved in 100 ml of dichloromethane is dropwise added 5.37 g (45.65×1.5 mmol) of acetyl chloride under ice-cooling, and the reaction mixture is stirred for an hour.

Dichloromethane (100 ml) is added thereto and the mixture is washed 7 times with water. The resulting mixture is dried over magnesium sulfate and evaporated to dryness under reduced pressure to give an oily product, which is purified through silica-gel chromatography (eluted with dichloromethane) to give 11.04 g of oily 2-acetoxymethyl-6,7-dichloro-2,3-dihydrobenzofuran, yield 93%.

Analysis Calcd (%) for C₁₁H₁₂O₂Cl₂: C, 53.46; H, 4.89; Cl, 28.69. Found (%): C, 53.28; H, 4.93; Cl, 28.90.

NMR (CDCl₃) δppm: 1.17 (t, 3H, J=7.0), 2.90–3.50 (m, 2H), 3.59 (q, 2H, J=7.0), 3.55 (d, 2H, J=5.0), 4.85–5.25 (m, 1H), 6.92 (s, 2H).

To a solution of 1 g of the oily 2-acetoxymethyl-6,7-dichloro-2,3-dihydrobenzofuran in 2 ml of thionyl chloride is added 1.25 ml of chlorosulfonic acid under ice-cooling and then stirred at room temperature for 2 hours. The reaction mixture is poured into iced water (about 50 g) and extracted with ether. The ether layer is washed water, then dried over calcium chloride, and evaporated to dryness under reduced pressure. To a solution of thus obtained oily product dissolved in 10 ml of dichloromethane is dropwise added 30% ethanol solution of dimethylamine (3.83×3 mmol) at −30° C., and the mixture is stirred for 2 hours. After the addition of dichloromethane, the reaction mixture is washed 10% hydrochloride. The dichloromethane layer is dried and then evaporated under reduced pressure to give an oily product, which is treated with ether to give the objective 2-acetoxymethyl-6,7-dichloro-5-(N,N-dimethylsulfamoyl)-2,3-dihydrobenzofuran (I h-70), yield 88%, m.p. 159°–160° C.

Analysis Calcd (%) for $C_{13}H_{15}NO_5Cl_2S$: C, 42.40; H, 4.11; N, 3.80; Cl, 19.26; S, 8.71. Found (%): C, 42.27; H, 4.05; N, 3.67; Cl, 19.49; S, 8.52.

NMR (CDCl$_3$) δppm: 2.08 (s, 3H), 2.90 (s, 6H), 2.95–3.70 (m, 2H), 4.34 (d, 2H, J=5.0), 5.06–5.45 (m, 1H), 7.85 (t, 1H, J=1.0).

EXAMPLES 71-76

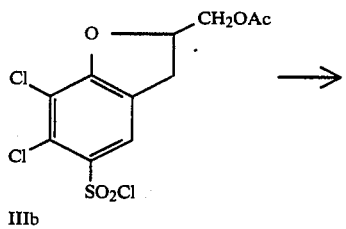

IIIb

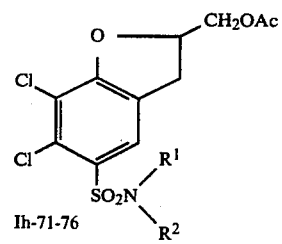

Ih-71-76

To a solution of 2-acetoxymethyl-5-chlorosulfonyl-6,7-dichloro-2,3-dihydrobenzofuran, which is prepared in the same manner as in Example 70, dissolved in 10 ml of dichloromethane is dropwise added an amine (3.83×3 mmol) and then stirred for 1 to 4.5 hours. After addition of dichloromethane, the reaction mixture is washed with 10% hydrochloric acid then with water. The dichloromethane layer is dried and evaporated under reduced pressure to give an oily product, which is crystallized from ether or chromatographed on silica gel [with dichloromethane or with dichloromethane/acetone (20/1) as an eluent] to give an objective one of the compounds I h-71 to 76. The reaction conditions and the physical properties of the compounds are summarized on Tables 5 and 6.

TABLE 5

| Compd. Ih | Substituent $R_1$ | $R_2$ | Reaction Conditions Temp. °C. | Time hr | Method for Purification | Yield (%) |
|---|---|---|---|---|---|---|
| 71 | H | H | −20 | 2 | Recrystallization from ether | 55 |
| 72 | CH$_3$ | CH$_2$—C$_6$H$_5$ | −30 | 2 | Recrystallization from ether | 75 |
| 73 | CH$_3$ | C$_6$H$_5$ | −30 | 2.5 | SiO$_2$—CH$_2$Cl$_2$ (Chromatography) | 55 |
| 74 | H | CH$_8$ | −30 | 1 | SiO$_2$—CH$_2$Cl$_2$, SiO$_2$—CH$_2$Cl$_2$/acetone (20:1) (Chromatography) | 55 |
| 75 | H | CH$_2$—C$_6$H$_5$ | −30 | 1.5 | SiO$_2$—CH$_2$Cl$_2$/acetone (20:1) (Chromatography) | 55 |
| 76 | H | C$_6$H$_5$ | −20 | 4.5 | SiO$_2$—CH$_2$Cl$_2$ (Chromatography) | 92 |

TABLE 6

| Compd. Ih | m.p. °C. | Molecular Formula (M.W.) | Elementary Analysis (%) C | H | N | S | Cl | NMR δ ppm (J Hz) |
|---|---|---|---|---|---|---|---|---|
| 71 | 164~166 | C$_{11}$H$_{11}$NO$_5$Cl$_2$S (340.181) | 38.84 38.64 | 23.26 3.11 | 4.12 4.07 | 9.43 9.25 | 20.84 21.03 | (d$_6$-acetone): 2.00 (3H, s), 3.07~3.77 (2H, m), 4.15~4.56 (2H, m), 5.16~5.53 (1H, m), 6.64 (2H, bs), 7.87 (1H, t, J = 1.2) |
| 72 | 106~107 | C$_{19}$H$_{18}$NSCl$_2$O$_5$· ½ H$_2$O (447.833) | 51.16 50.96 | 4.34 4.16 | 3.24 3.13 | 7.16 7.16 | 15.92 15.83 | (CDCl$_8$): 2.07 (3H, s), 2.75 (3H, s), 2.95~3.70 (2H, m), 4.35 (2H, d, J = 5.0), 4.32 (2H, s), 5.05~5.45 (1H, m), 7.35 (5H, s), 7.91 (1H, t, J = 1.0) |
| 73 | Oil | C$_{18}$H$_{17}$NSCl$_2$O$_5$ (430.310) | 50.24 49.98 | 3.98 3.99 | 3.26 3.16 | 7.45 7.25 | | (CDCl$_8$): 2.03 (3H, s), 2.80~3.60 (2H, m), 3.30 (3H, s), 4.27 (2H, d, J = 5.0), 5.00~5.37 (1H, m), 7.25 (5H, s), 7.64 (1H, t, J = 1.0) |
| 74 | 121~122 | C$_{12}$H$_{18}$NSCl$_2$O$_5$ (354.212) | 40.69 40.43 | 3.70 3.71 | 3.95 3.95 | 9.05 8.89 | 20.02 20.34 | (CDCl$_8$): 2.07 (3H, s), 2.60 (3H, d, J = 5.0), 3.00~3.70 (2H, m), 4.34 (2H, d, J = 5.0), 5.00 (1H, q, J = 5.0), 5.00~5.43 (1H, m), 7.86 (1H, t, J = 1.0) |
| 75 | 122~123 | C$_{18}$H$_{17}$NSCl$_2$O$_5$ (430.310) | 50.24 49.95 | 3.98 4.09 | 3.26 3.27 | 7.45 7.26 | 16.48 16.87 | (CDCl$_8$): 2.08 (3H, s), 2.90~3.60 (2H, m), 4.10 (2H, d, J = 6.0), 4.33 (2H, d, J = 5.0), 5.05~5.45 (2H, m), 7.24 (5H, s), 7.80 (1H, t, J = 1.0) |
| 76 | 169~170 | C$_{17}$H$_{15}$NSCl$_2$O$_5$· ½ H$_2$O (425.292) | 48.01 47.88 | 3.79 3.57 | 3.29 3.18 | 7.54 7.42 | | (CDCl$_8$): 1.97 (3H, s), 2.85~3.60 (2H, m), 4.25 (2H, d, J = 5.0), 4.95~5.30 (1H, m), 6.80~7.50 (1H, m), 7.13 (5H, s), 7.73 (1H, t, J = 1.0) |

EXAMPLE 77

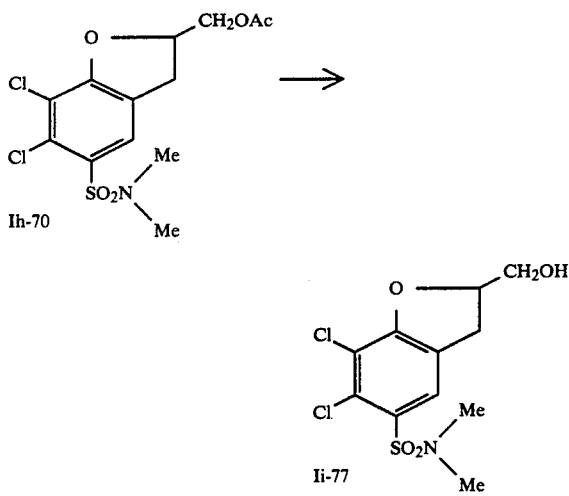

Ih-70

Ii-77

A mixture of 2.94 g of the compound I h-70 and a mixed solution of tetrahydrofuran (15 ml) with 5% sodium hydroxide (7.5 ml) is stirred at room temperature for 2 hours and 10 minutes. The reaction mixture turns transparent. After removal of the tetrahydrofuran by evaporation under reduced pressure, the reaction mixture is made acid by the addition of 10% hydrochloric acid, and extracted with ethyl acetate. The ethyl acetate layer is washed with water, dried, and evaporated under reduced pressure to give oily product, which is crystallized from ether and collected by filtration to give 2.15 g of the objective 6,7-dichloro-5-(N,N-dimethylsulfamoyl)-2-hydroxymethyl-2,3-dihydrobenzofuran (I i-77). This is recrystallized from ethyl acetate/ether to give its authentic specimen, yield 89%, m.p. 133°–134° C.

Analysis Calcd (%) for $C_{11}H_{13}NSCl_2O_4$: C, 40.50; H, 4.02; N, 4.29; S, 9.83; Cl, 21.74. Found (%): C, 40.32; H, 3.98; N, 4.21; S, 9.71; Cl, 21.56.

NMR (d$_6$-acetone) δppm: 2.85 (s, 6H), 3.00–4.10 (m, 4H), 4.20 (t, 1H, J=5.0), 5.00–5.35 (m, 1H), 7.80 (t, 1H, J=1.0).

EXAMPLES 78–83

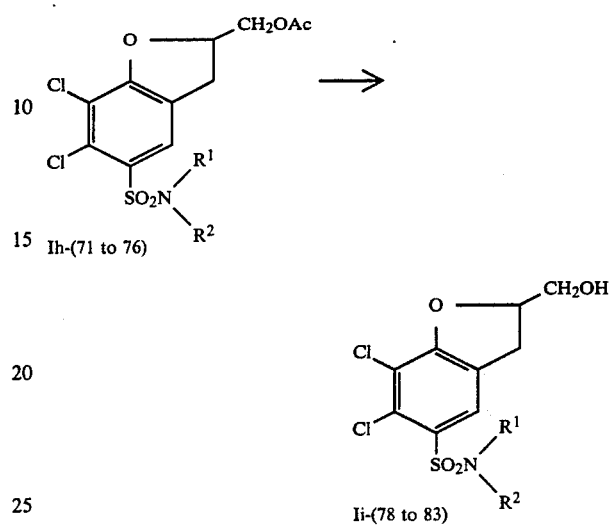

Ih-(71 to 76)

Ii-(78 to 83)

The compounds I h-71 to I h-76 are hydrolyzed in the same manner as in Example 77 to give the compounds I i-78 to I i-83, respectively corresponding to the compounds I h-71 to I h-76 in Table 5. The physical properties of the compounds are summarized on Table 7.

TABLE 7

| Compd. Ii | m.p. °C. | Molecular Formula (M.W.) | Elementary Analysis (%) | | | | | NMR δ ppm (J Hz) |
|---|---|---|---|---|---|---|---|---|
| | | | C | H | N | S | Cl | |
| 78 | 183~186 | C$_9$H$_9$NSCl$_2$O$_4$ (298.147) | 36.26<br>36.09 | 3.06<br>3.12 | 4.70<br>4.70 | 10.75<br>10.57 | 23.78<br>23.48 | (d$_6$-acetone): 3.13~4.17 (4H, m), 4.21 (1H, dd, J = 6.2 & 5.3), 5.00~5.35 (1H, m), 6.62 (2H, bs), 7.83 (1H, t, J = 1.2) |
| 79 | 73~74 | C$_{17}$H$_{17}$NSCl$_2$O$_4$·¼ H$_2$O (406.804) | 50.19<br>50.11 | 4.34<br>4.33 | 3.44<br>3.62 | 7.88<br>7.76 | | (CDCl$_3$): 2.35 (3H, s), 3.00~4.15 (4H, m), 4.38 (2H, s), 4.38 (1H, t, J = 7.0), 4.95~5.35 (1H, m), 7.35 (5H, s), 7.87 (1H, t, J = 1.0) |
| 80 | 117~118 | C$_{16}$H$_{15}$NSCl$_2$O$_4$ (388.273) | 49.50<br>49.46 | 3.89<br>3.79 | 3.61<br>3.50 | 8.26<br>8.26 | 18.26<br>18.18 | (d$_6$-acetone): 3.20~4.00 (4H, m), 3.37 (3H, s), 4.21 (1H, t, J = 6.0), 5.00~5.35 (1H, m), 7.31 (5H, s), 7.68 (1H, t, J = 1.0) |
| 81 | 118~119 | C$_{10}$H$_{11}$NSCl$_2$O$_4$ (312.174) | 38.48<br>38.36 | 3.55<br>3.50 | 4.49<br>4.41 | 10.27<br>10.00 | 22.71<br>22.72 | (d$_6$-acetone): 2.56 (3H, d, J = 6.0), 3.10~3.70 (2H, m), 3.60~4.00 (2H, m), 4.20 (1H, t, J = 7.0), 5.33~5.00 (1H, m), 6.42 (1H, b), 7.83 (1H, t, J = 1.0) |
| 82 | 55~56 | C$_{16}$H$_{15}$NSCl$_2$O$_4$·¼ H$_2$O (392.77) | 48.93<br>49.06 | 3.98<br>4.09 | 3.57<br>3.45 | 8.16<br>7.90 | 18.05<br>17.60 | (d$_6$-acetone): 3.00~3.60 (2H, m), 3.60~4.30 (2H, m), 4.25 (2H, d, J = 7.0), 5.00~5.35 (1H, m), 7.21 (5H, s), 7.73 (1H, t, J = 1.0) |
| 83 | 161~162 | C$_{15}$H$_{18}$NSCl$_2$O$_4$ (374.246) | 48.14<br>48.10 | 3.50<br>3.58 | 3.74<br>3.69 | 8.57<br>8.31 | 18.95<br>19.07 | (d$_6$-acetone): 2.40~5.20 (b), 3.15~4.05 (4H, m), 4.90~5.40 (1H, m), 6.70~7.40 (5H, m), 7.90 (1H, t, J = 1.0), 8.40~9.80 (1H, b) |

EXAMPLE 84

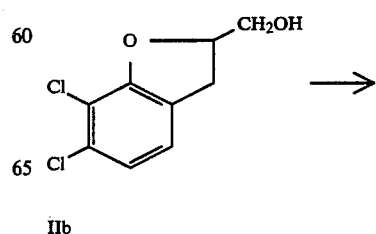

IIb

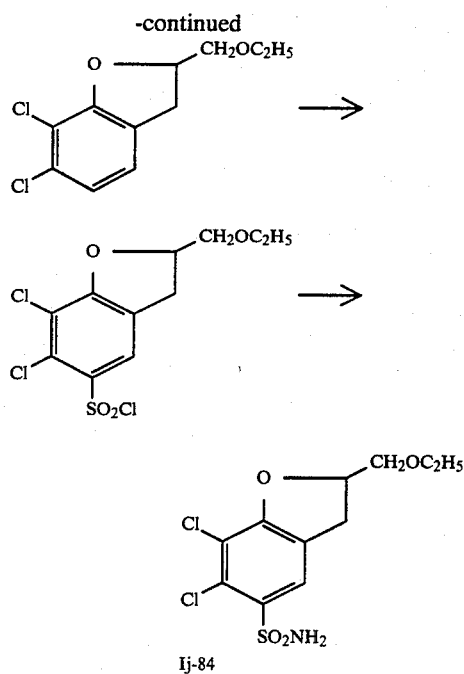

To a solution of 2.88 g of 6,7-dichloro-2-hydroxymethyl-2,3-dihydrobenzofuran dissolved in 22 ml of DMF is added 790 mg of sodium hydride (50% suspension) and stirred at room temperature for 30 minutes. After addition of 1.73 g of ethyl bromide, the reaction mixture is stirred at room temperature for 17 hours and extracted with water and ether. The ether layer is washed with water, dried over magensium sulfate, and evaporated under reduced pressure to give a residue, which is chromatographed on silica gel with dichloromethane as an eluent to give 2.0 g of oily 6,7-dichloro-2-ethoxymethyl-2,3-dihydrobenzofuran. To a solution of 2.0 g of the 6,7-dichloro-2-ethoxymethyl-2,3-dihydrobenzofuran dissolved in 5 ml of thionyl chloride is dropwise added 3 g of chlorosulfonic acid under ice-cooling. The reaction mixture is stirred at room temperature for 2 hours, then poured into iced water, and extracted with ethyl acetate. The ethyl acetate layer is washed with water, dried and evaporated under reduced pressure to give an oil, which is then dissolved in 30 ml of dichloromethane. After introduction of 30 ml of ammonia at −30° to −20° C., the mixture is allowed to stand at room temperature for a night and evaporated under reduced pressure to give an oily residue, which is then dissolved in ethyl acetate and washed with water. The ethyl acetate layer is dried and evaporated to dryness to give 2.7 g of an oily product, which is chromatographed on silica gel with dichloromethane (1000 ml) and successively dichloromethane/acetone (20/1) as eluents to give 900 mg of the objective 6,7-dichloro-2-ethoxymethyl-5-sulfamoyl-2,3-dihydrobenzofuran (I j-84) as crystals, yield 24%, m.p. 148°–149° C.

Analysis Calcd (%) for $C_{11}H_{13}NSCl_2O_4$: C, 40.50; H, 4.02; N, 4.29; S, 9.83; Cl, 21.74. Found (%): C, 40.37; H, 3.95; N, 4.22; S, 9.79; Cl, 21.50.

NMR (d$_6$-acetone) δppm: 1.12 (t, 3H, J=7.0), 3.05–3.75 (m, 2H), 3.71 (d, 2H, J=5.0), 5.05–5.45 (m, 1H), 6.60 (b, 2H), 7.82 (t, 1H, J=1.0).

EXAMPLE 85

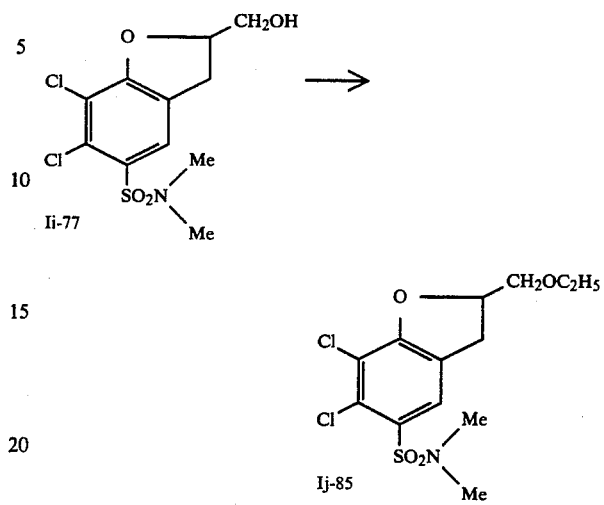

To a solution of 1 g (3.07 mmol) of 6,7-dichloro-(N,N-dimethylsulfamoyl)-2-hydroxymethyl-2,3-dihydrobenzofuran (I i-77) dissolved in 8 ml of DMF is added 200 mg (3.07×1.3 mmol) of sodium hydride (50% suspension) and stirred at room temperature for 30 minutes. After addition of 450 mg (3.07×1.3 mmol) of ethyl bromide, the reaction mixture is stirred at room temperature for 24 hours and combined with ether/water. The ether layer is washed twice with water, dried over magnesium sulfate, and evaporated under reduced pressure to give an oily product, which is chromatographed on silica gel [with dichloromethane and then dichloromethane/acetone (20/1) as eluents] to give 464 mg of the objective 6,7-dichloro-5-(N,N-dimethylsulfamoyl)-2-ethoxymethyl-2,3-dihydrobenzofuran (I j-85) as crystals, yield 43%, m.p. 91°–92° C.

Analysis Calcd (%) for $C_{13}H_{17}NSCl_2O_4$: C, 44.08; H, 4.84; N, 3.95; S, 9.05; Cl, 20.02. Found (%): C, 44.19; H, 4.87; N, 4.05; S, 8.82; Cl, 20.13.

NMR (CDCl$_3$) δppm: 1.20 (t, 3H, J=7.0), 8.87 (s, 6H), 3.10–3.15 (m, 2H), 3.60 (q, 2H, J=7.0), 3.70 (d, 2H, J=5.0), 5.00–5.35 (m, 1H), 7.83 (t, 1H, J=1.0).

EXAMPLE 86

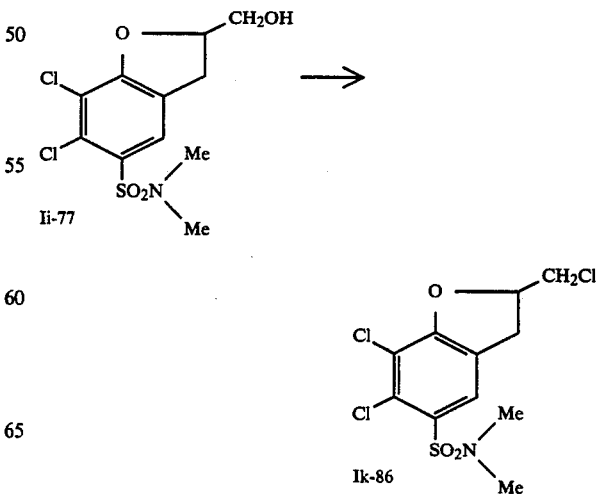

To a solution of 1 g of 6,7-dichloro-5-(N,N-dimethylsufamoyl)-2-hydroxymethyl-2,3-dihydrobenzofuran (I i-77) dissolved in 10 ml of pyridine is dropwise added 1 ml of thionyl chloride at 4° C. and the mixture stirred at room temperature for 21 hours. After addition of 10% hydrochloric acid the mixture is extracted with ethyl acetate (200 ml). The ethyl acetate layer is washed with further 10% hydrochloric acid and then water, dried over magnesium sulfate, and evaporated to dryness. The oily product left is chromatographed on silica gel (with dichloromethane as an eluent) to give 663 mg of the objective 2-chloromethyl-6,7-dichloro-5-(N,N-dimethylsulfamoyl)-2,3-dihydrobenzofuran (I k-86), yield 63%, m.p. 77°–78° C.

Analysis Calcd (%) for $C_{11}H_{12}NO_3Cl_3S$: C, 38.34; H, 3.51; N, 4.06; Cl, 30.86; S, 9.30. Found (%): C, 38.09; H, 3.54; N, 4.10; Cl, 30.63; S, 9.22.

NMR (CDCl$_3$) δppm: 2.87 (s, 6H), 3.05–3.85 (m, 2H), 3.81 (d, 2H, J=5.0), 5.10–5.45 (m, 1H), 7.85 (t, 1H, J=1.0).

The compound (I i-78) is reacted under the same conditions as above to give the following compound.

2-chloromethyl-6,7-dichloro-5-sulfamoyl-2,3-dihydrobenzofuran (I k-87), yield 66%, m.p. 195°–196° C.

Analysis Calcd (%) for $C_9H_8NO_3Cl_3S$: C, 34.14; H, 2.55; N, 4.42; Cl, 33.60; S, 10.13. Found (%): C, 34.09; H, 2.71; N, 4.40; Cl, 33.22; S, 10.20.

NMR (d$_6$-acetone) δppm: 3.15–3.90 (m, 2H), 3.85–4.20 (m, 2H), 5.15–5.60 (m, 1H), 6.67 (bs, 2H), 7.87 (t, 1H, J=1.0).

EXPERIMENT 1

Diuretic Effect on Rats

Test Method

Slc:SD 8-week-old rats (male, about 250 g bodyweight each) were used for the test. A few lumps of sugar in place of ordinary diets were given on the morning of the day before the test day and 5% glucose solution was given orally at a rate of 20 ml/kg in the evening (approximately at 4 p.m.) of the test day. In the morning for the test, a sample which was prepared by suspending or dissolving a test compound in 2% gum arabic was orally administered to each at a dose of 20 ml/kg. On the other hand, a mere 2% gum arabic was orally administered to the control group at 20 ml/kg. Immediately after the administration, the test animals were put in a plastic cage for the metabolic tests and their urine samples were collected for 5 hours. The cumulative urine volume, urinary sodium, and urinary potassium were quantitatively determined.

Test Results

Results on some typical compounds are shown in Table 8.

TABLE 8

| Compd. No. | Dose mg/Kg BW | Urine Volume ml/Kv BW | T/R (%) | Urinary Na$^+$ m eq./kg BW | T/R (%) | Urinary K$^+$ m eq./kg BW | T/R (%) |
|---|---|---|---|---|---|---|---|
| Ib-28 | 50 | 38.6 | 141 | 3.03 | 489 | 0.87 | 451 |
| " | 10 | 28.3 | 121 | 1.00 | 169 | 0.39 | 139 |
| Ib-30 | 50 | 39.7 | 163 | 3.01 | 602 | 1.13 | 452 |
| Ib-39 | 50 | 28.7 | 115 | 1.26 | 274 | 0.50 | 208 |
| Ii-78 | 50 | 43.4 | 158 | 3.27 | 529 | 0.74 | 444 |
| " | 10 | 28.0 | 120 | 1.06 | 180 | 0.33 | 118 |
| Ii-77 | 50 | 37.0 | 124 | 2.43 | 368 | 0.56 | 235 |
| Thienilic acid | 100 | 31.4 | 115 | 1.15 | 186 | 0.81 | 157 |
| Thienilic acid | 32 | 32.4 | 118 | 1.03 | 166 | 0.63 | 122 |

NOTE;
BW means "body weight".
T and R mean "Tested group" and "Referrence group", respectively.

EXPERIMENT 2

Diuretic Effect on Mice

Test Method

Slc:ddy 5-week-old mice (female, about 20 g bodyweight each) were used for the test. From the morning of the day before the test day, the mice were fasted but water. In the morning of the test day, a sample which was prepared by suspending or dissolving a test compound in 2% gum arabic was orally administered to each at 30 ml/kg. On the other hand, a mere 2% gum arabic was orally administered to the control group at 30 ml/kg. Immediately after the administration, 5 mice employed were put in a plastic cage for the metabolic tests and their urine samples were collected for 4 hours. The cumulative urine volume, urinary sodium, and urinary potassium were quantitatively determined.

Test Results

Results on some typical compounds as shown in Table 9.

TABLE 9

| Compd. No. | Dose mg/Kg BW | Urine Volume ml/Kg BW | T/R (%) | Urinary Na$^+$ m eq./kg BW | T/R (%) | Urinary K$^+$ m eq./kg BW | T/R (%) |
|---|---|---|---|---|---|---|---|
| Ib-28 | 30 | 48.4 | 186 | 4.74 | 912 | 1.19 | 220 |
| Ib-30 | 30 | 84.5 | 285 | 9.31 | 1058 | 2.14 | 297 |
| Ib-39 | 30 | 65.9 | 234 | 6.66 | 793 | 1.88 | 232 |
| Ii-78 | 30 | 35.4 | 126 | 2.62 | 460 | 1.27 | 212 |
| Ii-77 | 30 | 25.6 | 96 | 3.26 | 466 | 0.90 | 191 |
|  | 30 | 36.4 | 236 | 3.85 | 535 | 1.19 | 189 |

EXPERIMENT 3

Hyperuricosuric Effect on Rats

Nine-week-old male rats were employed for the test. Potassium oxonate was intraperitoneally administered to the animals at a dose of 250 mg/kg in order to measure uric acid clearance and inulin clearance. Within 2 hours after the administration of the potassium oxonate, canulae were placed into the right femoral artery, left femoral vein, and urinary bladder of each animal under anesthesia with pentobarbital for collection of the blood, infusion of the drug, and collection of urine, respectivelly. Exact 2 hours after the first administration, potassium oxanate was administered again at the same dosage and then 60% urethane (2 ml/kg) and 15% inulin (4 ml/kg) were subcutaneously injected. A mixture of 4% mannitol/1.5% inulin/0.9% saline was infused at the flow rate of 0.1 ml/min. to the animal on a plate kept at 30° C. After the equilibrium for 40 minutes, arterial blood (0.2 ml each) samples were collected 6 times every 20 minutes, and five 20-minutes urines were collected. Immediately after the collection of every blood sample, the serum was separated therefrom, and the serum samples and the urine samples were stored in a refregirater.

Immediately after the first collection of the urine sample, a test compound suspended in 1% gum arabic was intraperitoneally administered at 2 ml/kg.

Uric acid both in the serum and in the urine was quantitatively analyzed by the method of Yonetani et al's. [Yonetani, Y.; Ishii, M.; Iwaki, K., Japanese Pharmacology 30, 829–840 (1980)]. Inulin was also done substantially by the method of Vurek's and Pegram's [Vurek, G. G., Pegram, S. E., Anal. Biochem. 16, 409–419 (1966)]. In order to analyze uric acid, 0.1 ml of diluted solution of deprotenized serum or urine was admixed with 1% dimedon/orthoric acid solution and the resulting mixture was heated for 5 minutes. The mixture was then cooled in ice-cold water, combined with 2.0 ml of acetic acid, and the fluorescence was measured at 410 nm in the excitation wave length at 360 nm.

Test Results

Results on some typical compounds are shown in Table 10.

As clearly learned from the foregoing experiments, the compounds of this invention have a significant diuretic with uricosuric activity and, therefore, can be applied as a diuretic antihypertensive for the treatment or the prophylaxis of essential or renal hypertension, nephredema, cardiac or hepatic edema, gestosis, or the like disease.

The compounds of this invention may be administered orally or parenterally (intravenously or intramuscularly) in a suitable form such as tablets, granules, fine granules, powders, capsules, injections or the like formulations. They can be administered orally at a single or a separate daily-dosage of 0.5–200 mg, preferably 1–100 mg; or parenterally at 0.01–50 mg, preferably at 0.1–20 mg.

TABLE 10

| Compd. No. | Dose mg/Kg BW | U V[1] max[4] (ml/min. Kg BW) | U V[1] increase[5] (%) | U ua V[2] max[4] (ml/min. Kg BW) | U ua V[2] increase[5] (%) | F E ua[3] max[4] | F E ua[3] increase[5] (%) |
|---|---|---|---|---|---|---|---|
| Ib-28 | 50 | 1.04 | 130 | 0.26 | 78 | 0.99 | 33 |
| Ib-29 | 50 | 0.88 | 48 | 0.33 | 110 | 1.08 | 70 |
| Ib-30 | 50 | 0.94 | 111 | 0.20 | 35 | 0.86 | 15 |
| Ib-33 | 50 | 0.68 | 42 | 0.34 | 41 | 0.79 | 10 |
| Ib-38 | 50 | 0.86 | 65 | 0.27 | 50 | 0.82 | 20 |
| Ib-39 | 50 | 0.67 | 45 | 0.28 | 83 | 0.93 | 33 |
| Ib-41 | 50 | 1.08 | 139 | 0.22 | 99 | 1.04 | 50 |
| Ib-42 | 50 | 0.97 | 125 | 0.24 | 74 | 1.06 | 56 |
| Ib-51 | 50 | 0.82 | 59 | 0.39 | 66 | 1.14 | 35 |
| Ic-56 | 50 | 0.56 | 60 | 0.20 | no change | 0.72 | 16 |
| Ic-59 | 50 | 1.06 | 115 | 0.24 | 16 | 0.77 | 8 |
| Id-62 | 50 | 0.47 | 29 | 0.18 | 31 | 0.76 | 20 |
| Ii-77 | 50 | 0.52 | 81 | 0.30 | 124 | 0.88 | 33 |
| Ii-78 | 50 | 0.43 | 20 | 0.23 | 36 | 0.87 | 26 |
| Thienilic acid | 100 | 0.37 | 9 | 0.37 | 70 | 0.74 | 8 |
| Referrence[6] | 0 | 0.30 | 0 | 0.19 | 0 | 0.66 | 0 |

[1]Urine Volume
[2]Urinary uric acid
[3]Fractional excretion of uric acid: Uric acid clearance/inulin clearance
[4]Maximum among the 4 measurements after administration
[5]Increase (%) of mean value of the 4 measurements after administration to that of before administration
[6]Only 1% gum arabic solution, in which test compound is to be suspended, was used.

What is claimed is:

1. A compound represented by the following formula:

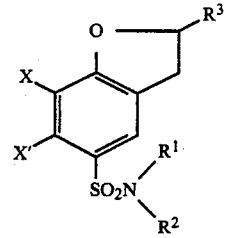

and the pharmaceutically acceptable salts thereof, wherein
   $R^1$ and $R^2$ are the same or different from each other, and each is hydrogen, lower alkyl, 4- to 7-membered cycloalkyl, phenyl substituted by halo or alkoxy, unsubstituted phenyl, phenyl(lower alkyl), lower alkoxycarbonyl, or morpholino(lower alkyl); or
   $NR'R^2$ represents lower alkyl substituted or unsubstituted pyrrolidine, piperidine or morpholino,
   $R^3$ is a group represented by $COR^4$ or $CH_2R^5$,
   $R^4$ is hydroxy or a group represented by $OR^6$ or $NR^7R^8$,
   $R^5$ is hydroxy, lower alkoxy, lower aliphatic acyloxy, or halogen,
   $R^6$ is lower alkyl, aryl, carboxymethyl or a lower alkyl ester thereof, hydroxymethyl or a lower aliphatic acylate thereof, or 3-phthalidyl,
   $R^7$ and $R^8$ are the same or different from each other, and each is hydrogen or lower alkyl, and X and X' are the same or different from each other, and each is hydrogen or halogen and a pharmaceutically acceptable carrier.

2. A compound claimed in claim 1, wherein X and X' each is chlorine, and the salt thereof.

3. A compound claimed in claim 1, wherein $R^3$ is carboxy, and the salt thereof.

4. A compound claimed in claim 1, wherein $R^3$ is hydroxymethyl, and the salt thereof.

5. A compound claimed in claim 1, wherein both $R^1$ and $R^2$ are hydrogen, methyl, or ethyl, and the salt thereof.

6. An antihypertensive diuretic agent containing an antihypertensive effective amount of a compound represented by the following formula:

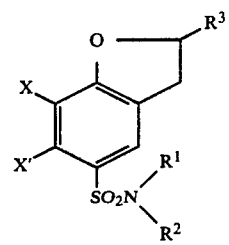

or a pharmaceutically acceptable salt thereof as an active ingredient, wherein
$R^1$ and $R^2$ are the same or different from each other, and each is hydrogen, lower alkyl, 4- to 7-membered cycloalkyl, phenyl substituted by halo or alkoxy or unsubstituted phenyl, phenyl(lower alkyl), lower alkoxycarbonyl, or morpholino(lower alkyl); or
NR'R² represents lower alkyl substituted or unsubstituted pyrrolidine, piperidine or morpholino,
$R^3$ is a group represented by $COR^4$ or $CH_2R^5$,
$R^4$ is hydroxy or a group represented by $OR^6$ or $NR^7R^8$,
$R^5$ is hydroxy, lower alkoxy, lower aliphatic acyloxy, or halogen,
$R^6$ is lower alkyl, aryl, carboxymethyl or a lower alkyl ester thereof, hydroxymethyl or a lower aliphatic acylate thereof, or 3-phthalidyl,
$R^7$ and $R^8$ are the same or different from each other, and each is hydrogen or lower alkyl, and
X and X' are the same or different from each other, and each is hydrogen or halogen and an inert pharmaceutically acceptable carrier.

* * * * *